(12) United States Patent
Matsumura et al.

(10) Patent No.: US 8,361,691 B2
(45) Date of Patent: Jan. 29, 2013

(54) RADIATION-SENSITIVE COMPOSITION AND PROCESS FOR PRODUCING LOW-MOLECULAR COMPOUND FOR USE THEREIN

(75) Inventors: Nobuji Matsumura, Tokyo (JP); Daisuke Shimizu, Tokyo (JP); Toshiyuki Kai, Tokyo (JP)

(73) Assignee: JSR Corporation, Tokyo (JP)

( * ) Notice: Subject to any disclaimer, the term of this patent is extended or adjusted under 35 U.S.C. 154(b) by 44 days.

(21) Appl. No.: 12/439,860

(22) PCT Filed: Aug. 28, 2007

(86) PCT No.: PCT/JP2007/066644
§ 371 (c)(1),
(2), (4) Date: Mar. 4, 2009

(87) PCT Pub. No.: WO2008/029673
PCT Pub. Date: Mar. 13, 2008

(65) Prior Publication Data
US 2009/0280433 A1    Nov. 12, 2009

(30) Foreign Application Priority Data

Sep. 8, 2006   (JP) ................................ 2006-243563

(51) Int. Cl.
G03F 7/004 (2006.01)
G03F 7/039 (2006.01)
C07C 309/12 (2006.01)
C07C 381/12 (2006.01)
C07C 69/96 (2006.01)
H01L 21/027 (2006.01)

(52) U.S. Cl. ........... 430/270.1; 522/31; 522/55; 522/52; 522/63; 558/270

(58) Field of Classification Search .................. None
See application file for complete search history.

(56) References Cited

U.S. PATENT DOCUMENTS

| | | | |
|---|---|---|---|
| 4,957,988 A * | 9/1990 | Irving et al. | 526/259 |
| 5,191,124 A | 3/1993 | Schwalm et al. | |
| 5,260,410 A | 11/1993 | Schwalm | |
| 5,556,734 A * | 9/1996 | Yamachika et al. | 430/270.1 |
| 5,641,604 A * | 6/1997 | Sinta et al. | 430/192 |
| 5,679,496 A | 10/1997 | Ohsawa et al. | |
| 5,824,824 A | 10/1998 | Osawa et al. | |
| 6,497,473 B2 * | 12/2002 | Kim | 347/33 |
| 2006/0166135 A1 | 7/2006 | Wada | |
| 2006/0188810 A1 | 8/2006 | Ohsawa et al. | |
| 2006/0275695 A1 * | 12/2006 | Jung et al. | 430/270.1 |
| 2007/0117043 A1 * | 5/2007 | Gonsalves | 430/270.1 |
| 2007/0122734 A1 * | 5/2007 | Roberts et al. | 430/270.1 |
| 2007/0141512 A1 | 6/2007 | Wada et al. | |
| 2007/0231708 A1 | 10/2007 | Matsumaru et al. | |
| 2008/0113294 A1 * | 5/2008 | Echigo et al. | 430/270.1 |

FOREIGN PATENT DOCUMENTS

| | | |
|---|---|---|
| JP | 8-160606 | 6/1996 |
| JP | 8-248626 | 9/1996 |
| JP | 9-12537 | 1/1997 |
| JP | 10-7650 | 1/1998 |
| JP | 10-83073 | 3/1998 |
| JP | 10-120610 | 5/1998 |
| JP | 10-182603 A * | 7/1998 |
| JP | 10-310545 | 11/1998 |
| JP | 11-322656 | 11/1999 |
| JP | 2000-305270 | 11/2000 |
| JP | 2003-183227 | 7/2003 |
| JP | 2003-321423 | 11/2003 |
| JP | 2005-189501 | 7/2005 |
| JP | 2006-512600 | 4/2006 |
| JP | 2006-201711 | 8/2006 |
| JP | 2006-227331 | 8/2006 |
| JP | 2007-199692 | 8/2007 |
| WO | WO 03/107093 A2 * | 12/2003 |
| WO | WO 2004053594 | 6/2004 |
| WO | WO 2006/013687 | 2/2006 |
| WO | WO-2006/068267 A1 * | 6/2006 |

OTHER PUBLICATIONS

Complete machin e translation of JP 2005-189501 a generated Dec. 14, 2010, 60 pages.*
English translation of JP, 10-182603, A (1998) from machine translation from AIPN Japan Patent Office National Center for Industrial Property Information and Training, generated Jan. 22, 2012, 10 pages.*
Kunz et al, "Outlook for 157 nm resist design", J. Vac. Sci. Technol. B 17(6), Nov./Dec. 1999, American Vacuum Society, pp. 3267-3273.*
Hiroshi Ito, Gregory Breyta, Donald C. Hofer, Thomas Fischer, and R. Bruce Prime Proc. SPIE 2438, 53 (1995); doi:10.1117/12.210353 |Online Publication Date: Apr. 5, 2005.*
Extended European Search Report for corresponding EP Application No. 07793084.0-1226, Apr. 6, 2011.

* cited by examiner

*Primary Examiner* — Cynthia Hamilton
(74) *Attorney, Agent, or Firm* — Ditthavong Mori & Steiner, P.C.

(57) ABSTRACT

A radiation-sensitive composition contains (A) a low-molecular-weight compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, and (B) a solvent.

4 Claims, No Drawings

RADIATION-SENSITIVE COMPOSITION AND PROCESS FOR PRODUCING LOW-MOLECULAR COMPOUND FOR USE THEREIN

TECHNICAL FIELD

The present invention relates to a radiation-sensitive composition suitably used for super-micro lithography processes such as production of ultra-LSIs and high capacity microchips, and for other photofabrication processes, and to a process for producing a low-molecular-weight compound for use therein.

BACKGROUND ART

Lithographic microfabrication using a photoresist composition has been employed in processes for producing semiconductor devices such as ICs and LSIs. Due to increased integration of integrated circuit boards in recent years, super-micro patterns in the order of submicron or quarter micron are being demanded. Along with this tendency, the wavelength of radiation used for exposure tends to be shortened to g-lines, and i-lines, and further to a KrF excimer laser. At the present time, in addition to the lithographic process using excimer lasers, lithographic processes using electron beams, X-rays, or EUV-rays are being developed.

Electron beam lithography is particularly expected as a pattern forming technology of the next generation or the next-next generation. Development of a positive-tone resist exhibiting high sensitivity and high resolution is also desired. Increasing the sensitivity is very important in order to reduce the time required for wafer processing. However, increasing sensitivity of a positive-tone resist for use with electron beams not only decreases resolution, but also tends to cause line edge roughness. For this reason, development of a resist which can satisfy properties such as sensitivity, resolution, and line edge roughness at the same time is strongly desired.

The line edge roughness refers to roughness of the edge on the interface of the resist pattern and the substrate. That is, the edge on the interface of the resist pattern and the substrate irregularly fluctuates in the direction vertical to the line direction due to the properties of the resist. When the pattern is viewed from directly above, the edge is seen to have irregularity. Since the irregularity is transferred in the etching step in which the resist is used as a mask, the electrical properties deteriorate and the yield is decreased. Improvement of line edge roughness is very important particularly in a ultra-micro region of 0.25 µm or less. High sensitivity, high resolution, good pattern form, and good line edge roughness are in a trade-off relationship, and satisfying these properties at the same time is a very important subject. Satisfying high sensitivity, high resolution, and the like is also very important also in lithography using X-rays and EUV-rays.

As a resist suitable for a lithography process using electron beams, X-rays, or EUV-rays, chemically amplified resists which mainly use an acidic catalyst reaction are used from the viewpoint of high sensitivity. In a positive-tone resist, a chemically-amplified resist composition containing a phenolic polymer, which is insoluble or scarcely soluble but becomes soluble in an alkaline aqueous solution by the action of an acid (acid-dissociable phenolic resin), and an acid generator as main components is effectively used.

As such an acid-dissociable phenolic resin, a phenol compound derivative having a specific structure (Patent Documents 1 to 3), a calixarene having a specific structure (Patent Documents 4 and 5), a calix resorcin arene (Patent Documents 5 and 6), a phenolic dendrimer having a calix resorcin arene as a mother nucleus (Patent Document 7), and the like have been disclosed. Resist compositions in which these compounds are used have also been disclosed.

However, no combination of the above-described resins has been successful in achieving high sensitivity, high resolution, good pattern form, and good line edge roughness at the same time.

Patent Document 1: JP-A-10-83073
Patent Document 2: JP-A-2000-305270
Patent Document 3: JP-A-2003-183227
Patent Document 4: JP-A-10-120610
Patent Document 5: JP-A-11-322656
Patent Document 6: JP-A-2003-321423
Patent Document 7: JP-A-10-310545

DISCLOSURE OF THE INVENTION

The present invention has been achieved in view of such problems in general technologies and has an object of providing a radiation-sensitive composition exhibiting high sensitivity, high resolution, good pattern form, and good line edge roughness at the same time. Another object of the present invention is to provide a process for producing a low-molecular-weight compound which can provide a radiation-sensitive composition satisfying high sensitivity, high resolution, good pattern form, and good line edge roughness at the same time.

The inventors of the present invention have conducted extensive studies in order to achieve the above objects. As a result, the inventors have found that the above object can be achieved by using a low-molecular-weight compound having one or more acid-dissociable groups and one or more radiation-sensitive acid generating groups in one molecule and having a number-average molecular weight (Mn) in a specific range. This finding has led to the completion of the present invention.

Specifically, the following radiation-sensitive compositions and processes for producing the low-molecular-weight compound are provided according to the present invention.

[1] A radiation-sensitive composition, comprising; (A) a low-molecular-weight compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, and (B) a solvent.

[2] The radiation-sensitive composition according to [1], wherein the low-molecular-weight compound (A) is obtained by condensing a compound having at least one of a phenolic hydroxyl group and a carboxyl group with an onium salt by etherification or esterification in the presence of at least one selected from the group consisting of an acid, a base, and a dehydrating agent.

[3] The radiation-sensitive composition according to [1], wherein the low-molecular-weight compound (A) is obtained by reacting a compound having at least one of a phenolic hydroxyl group and a carboxyl group with an N-hydroxydicarboxylmide compound in the presence of a base.

[4] The radiation-sensitive composition according to [1], wherein the low-molecular-weight compound (A) is obtained by reacting a compound having at least one of an N-hydroxydicarboxylmide group, a phenolic hydroxyl group, and a carboxyl group with a halogenated sulfonyl compound in the presence of a base.

[5] The radiation-sensitive composition according to any one of [1] to [4], wherein the low-molecular-weight compound (A) is a compound shown by the following formula (1),

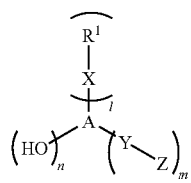
(1)

wherein A represents an aliphatic group having 1 to 50 carbon atoms, an aromatic group having 6 to 50 carbon atoms, an organic group containing the aliphatic group and the aromatic group at the same time, or a group having a valence of (l+m+n) in which the aliphatic group, the aromatic group, and the organic group are repeated; X represents —O—, —CH$_2$C(=O)—O—, —C(=O)—O—, or —Ar—O— (wherein Ar represents a 1,4-phenylene group); R$^1$ represents an acid-dissociable group which is a substituted or unsubstituted tertiary hydrocarbon group having 4 to 12 carbon atoms or a substituted or unsubstituted acetal group; Y represents a single bond, —R$^2$—, —CH$_2$—C(=O)—O—R$^2$—, —C(=O)—O—R$^2$—, or —Ar—O—R$^2$— (wherein R$^1$ represents a substituted or unsubstituted methylene group or a substituted or unsubstituted alkylene group having 2 to 30 carbon atoms, and Ar represents a substituted or unsubstituted 1,4-phenylene group); l is an integer from 1 to 4; m is an integer from 1 to 3; n is an integer from 0 to 10; Z is an organic group shown by any one of the following formulas (2) to (5) and, when m is 2 or 3, the organic groups may be either the same or different,

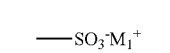
(2)

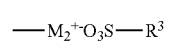
(3)

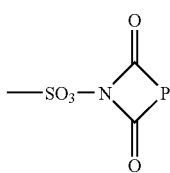
(4)

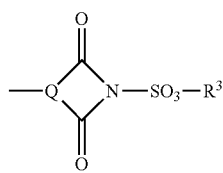
(5)

wherein M$_1^+$ in the formula (2) represents a monovalent onium cation, M$_2^+$ in the formula (3) represents a monovalent onium cation, R$^3$ in the formula (3) and the formula (5) represents a substituted or unsubstituted alkyl group or a substituted or unsubstituted aryl group having 1 to 15 carbon atoms, P in the formula (4) represents a substituted or unsubstituted alkylene group or a substituted or unsubstituted arylene group having 2 to 10 carbon atoms, and Q in the formula (5) represents a group shown by any one of the following formulas (6) to (8):

(6)

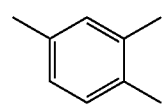
(7)

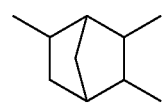
(8)

[6] The radiation-sensitive composition according to [5], wherein the content of the low-molecular-weight compound (A) is 80 mass % or more of the 100 mass % of the total solid component.

[7] The radiation-sensitive composition according to [5], further comprising an acid diffusion controller.

[8] A process for producing a low-molecular-weight compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, comprising; obtaining the low-molecular-weight compound by condensing a compound having at least one of a phenolic hydroxyl group and a carboxyl group with an onium salt by etherification or esterification in the presence of at least one selected from the group consisting of an acid, a base, and a dehydrating agent.

[9] A process for producing a low-molecular compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, comprising; obtaining the low-molecular compound by reacting a compound having a halogenated sulfonyl group and at least one of a phenolic hydroxyl group and a carboxyl group with a N-hydroxydicarboxylmide compound in the presence of a base.

[10] A process for producing a low-molecular compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, comprising; obtaining the low-molecular compound by reacting a compound having an N-hydroxydicarboxylmide group and at least one of a phenolic hydroxyl group and a carboxyl group with a halogenated sulfonyl compound in the presence of a base.

The radiation-sensitive composition of the present invention has an effect of satisfying high sensitivity, high resolution, good pattern form, and good line edge roughness at the same time.

According to the process for producing a low-molecular-weight compound of the present invention, a low-molecular-weight compound which can provide a radiation-sensitive composition satisfying high sensitivity, high resolution, good pattern form, and good line edge roughness at the same time can be produced using a simple and easy method.

BEST MODE FOR CARRYING OUT THE INVENTION

The preferred embodiments for carrying out the present invention are described below. However, the present invention is not restricted to the following embodiments and it should be construed that there are also included, in the present invention, those embodiments in which appropriate changes, improvements, etc. have been made to the following embodiments based on the ordinary knowledge possessed by those skilled in the art, as long as there is no deviation from the gist of the present invention.
(Radiation-Sensitive Composition)

One of the embodiments of the present invention is a radiation-sensitive composition which comprises (A) a low-molecular-weight compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, and (B) a solvent. The details are described below.
((A) Low-Molecular-Weight Compound)

The low-molecular-weight compound (A) contained in the radiation-sensitive composition of the present invention has one or more acid-dissociable groups which are decomposed by the action of an acid in one molecule. The acid-dissociable group has an effect of being dissociated (decomposed) by the action of an acid and enhancing solubility of the radiation-sensitive composition in which the low-molecular-weight compound is used in an alkaline developing solution. Specific examples of the acid-dissociable group are described later.

The low-molecular-weight compound (A) has one or more radiation-sensitive acid generating groups which generate an acid by being irradiated with an active ray or radiation in one molecule. The acid generated from the radiation-sensitive acid generating group has an effect of acting on and dissociating (decomposing) the acid-dissociable group. Specific examples of the radiation-sensitive acid generating group are described later.

The polystyrene-reduced number-average molecular weight (Mn) of the low-molecular-weight compound (A) measured by gel permeation chromatography (GPC) is 500 to 4,000, preferably 700 to 3,500, and more preferably 800 to 3,500. If the Mn is below 500, the baking temperature such as PB and PEB is limited and resolution may be impaired. If the Mn exceeds 4,000, the line edge roughness may be impaired. The low-molecular-weight compound (A) is a single-molecule compound having a comparatively low molecular weight. And the low-molecular-weight compound (A) is neither a polymer nor a resin which is obtained from a compound (monomer) having an unsaturated bond by causing the bonds to continuously grow in a chain-like manner by cleaving the unsaturated bonds using an initiator.

As a preferable example of the low-molecular-weight compound (A), a compound having the chemical structure shown by the following formula (1) can be given,

wherein A represents an aliphatic group having 1 to 50 carbon atoms, an aromatic group having 6 to 50 carbon atoms, an organic group containing an aliphatic group and aromatic group at the same time, or a group having a valence of (l+m+n) in which the aliphatic group, the aromatic group, and the organic group are repeated; l is an integer from 1 to 4; m is an integer from 1 to 3; and n is an integer from 0 to 10. As specific examples of A in the formula (1), the groups of the following formulas (1-1) to (1-93) can be given.

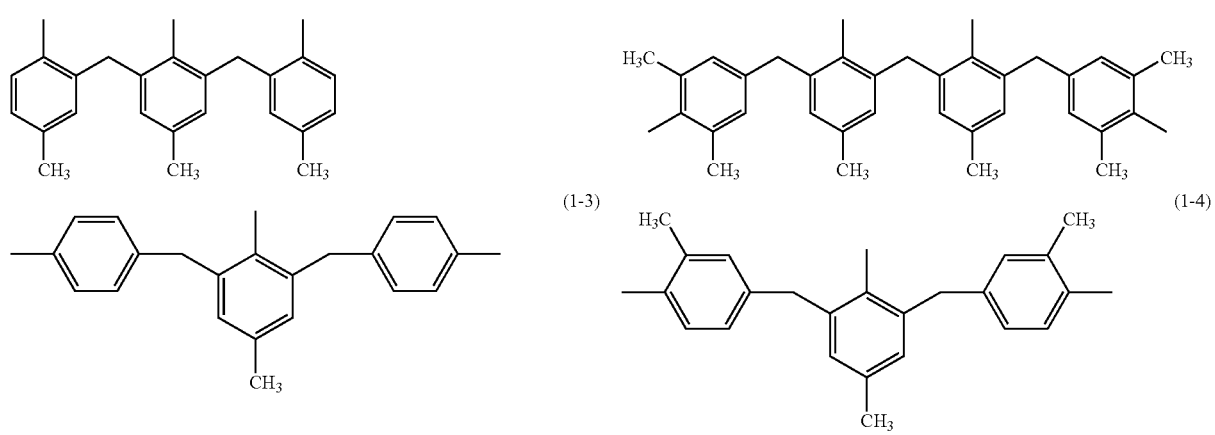

-continued
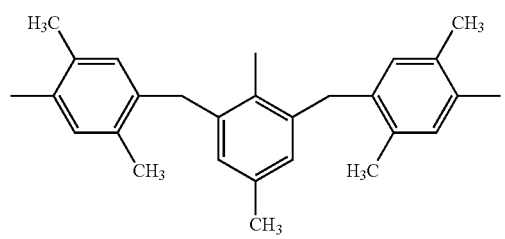
(1-5)
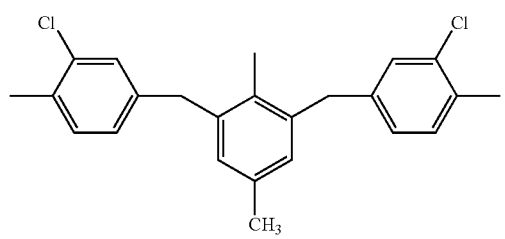
(1-6)
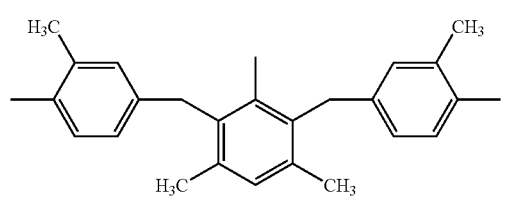
(1-7)
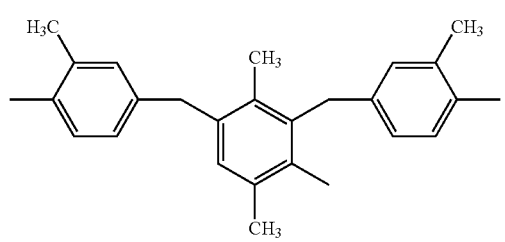
(1-8)
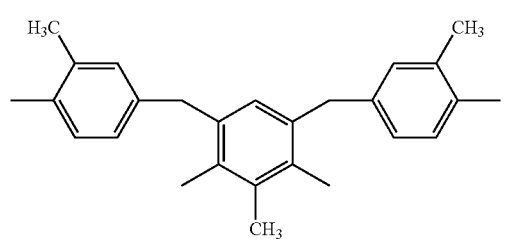
(1-9)
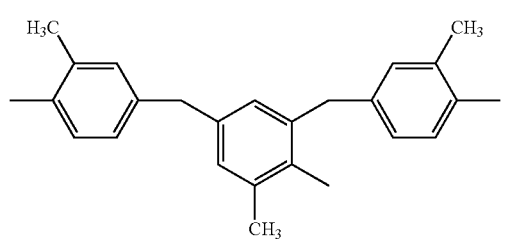
(1-9)
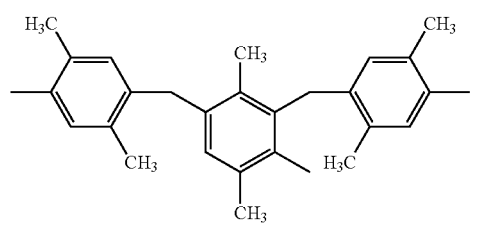
(1-10)
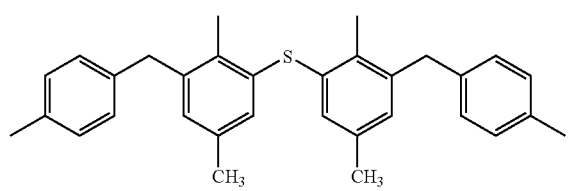
(1-11)
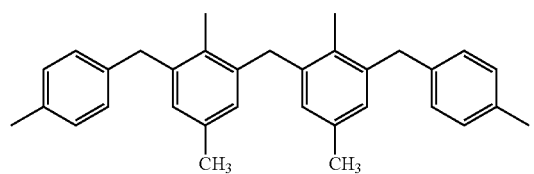
(1-12)
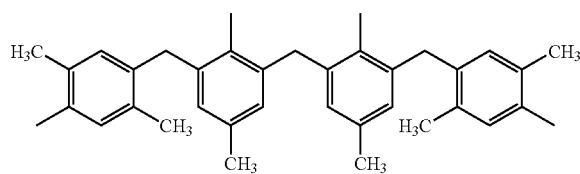
(1-13)
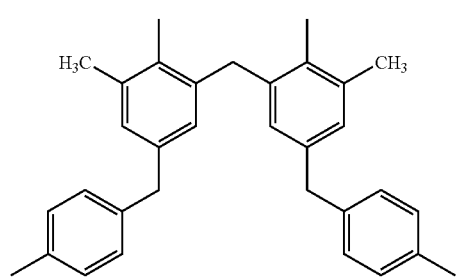
(1-14)
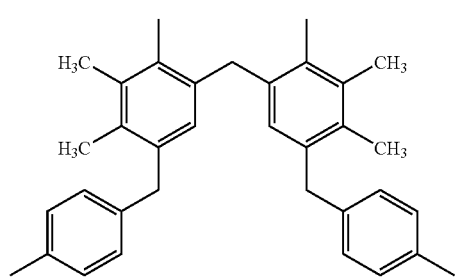
(1-15)

-continued
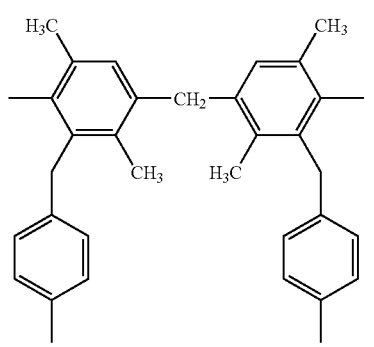
(1-16)
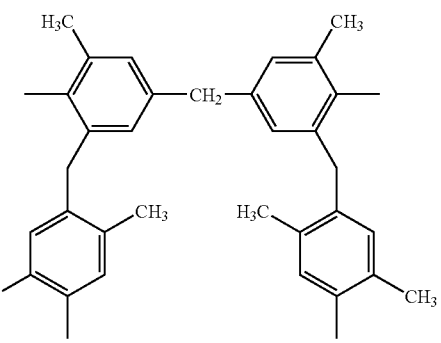
(1-17)
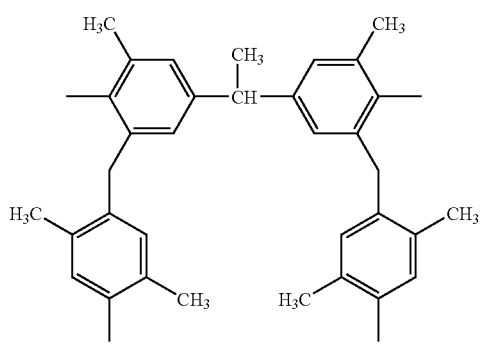
(1-18)
(1-19)
(1-20)
(1-21)
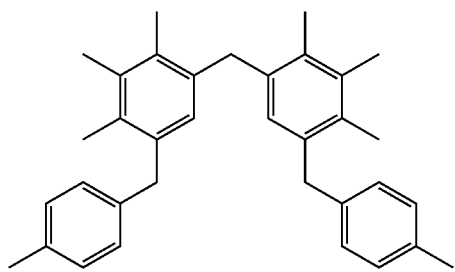
(1-22)
(1-23)
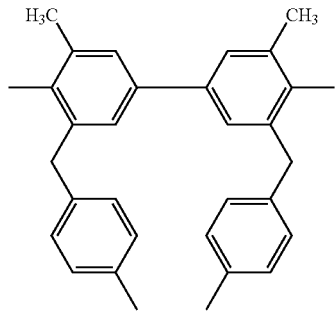
(1-24)
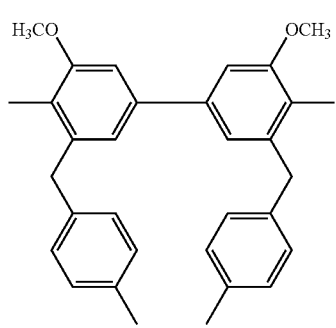
(1-25)

-continued
(1-26)
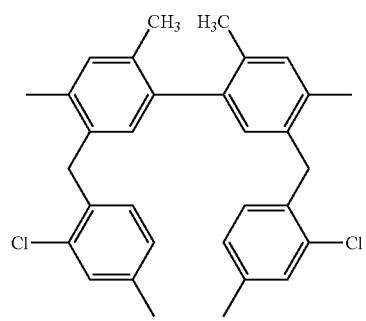
(1-27)
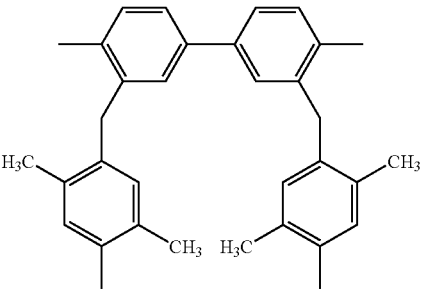
(1-28)
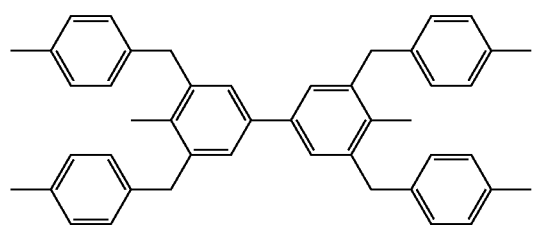
(1-29)
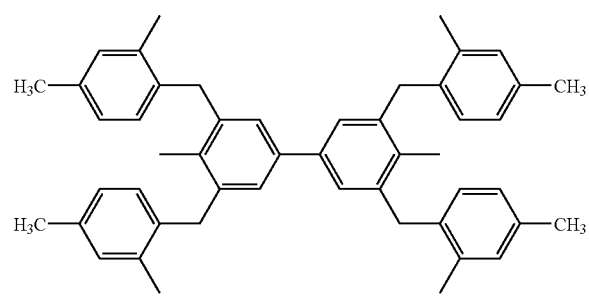
(1-30)
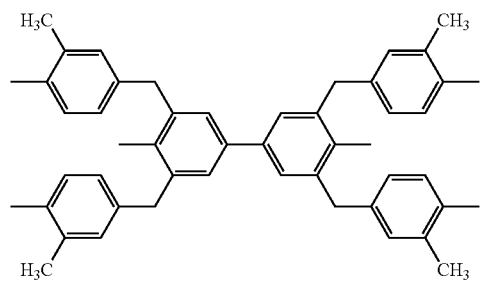
(1-31)
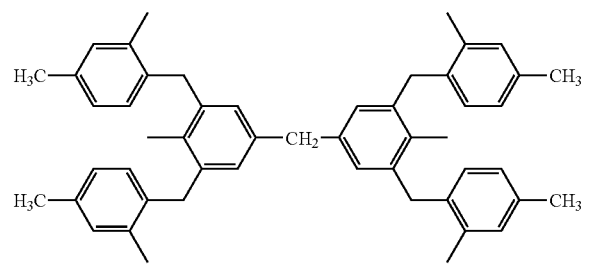
(1-32)
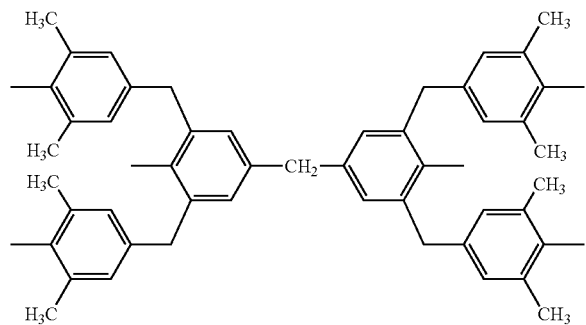
(1-33)
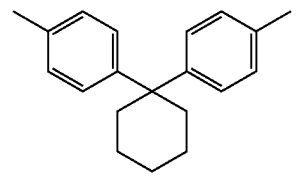
(1-34)
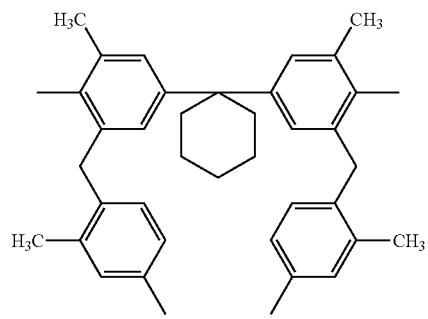
(1-35)
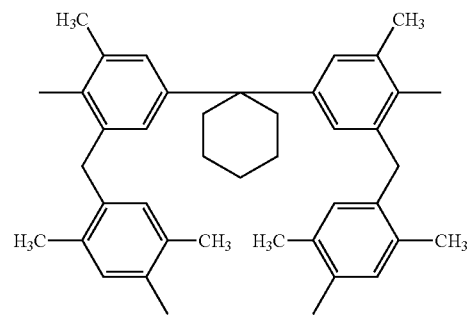

-continued
(1-36)
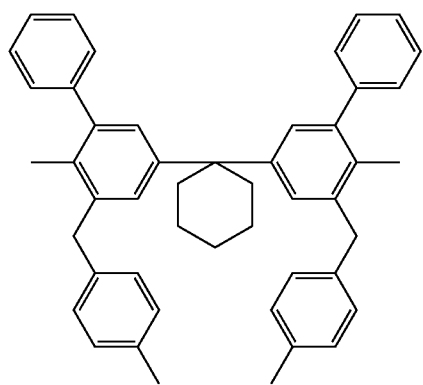
(1-37)
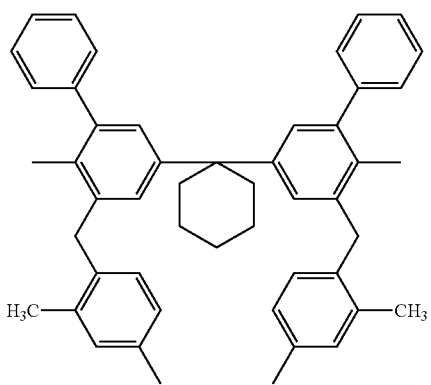
(1-38)
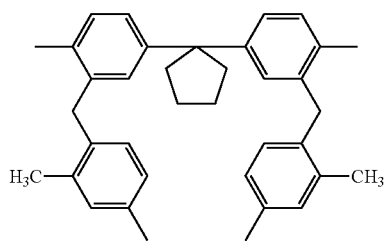
(1-39)
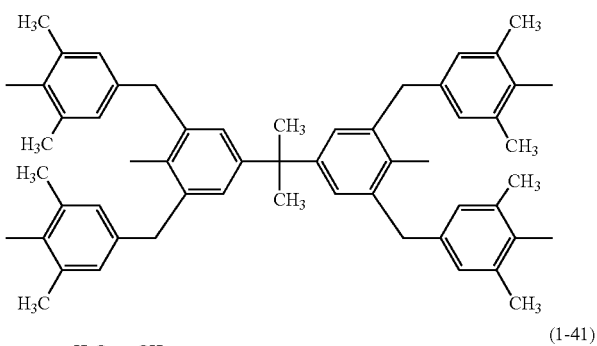
(1-40)
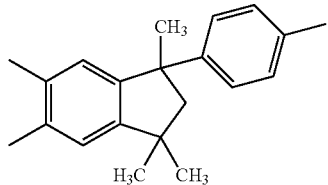
(1-41)
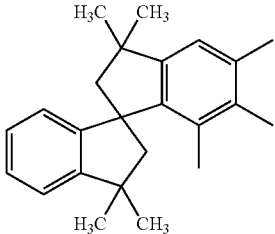
(1-42)
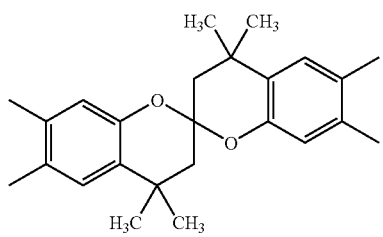
(1-43)
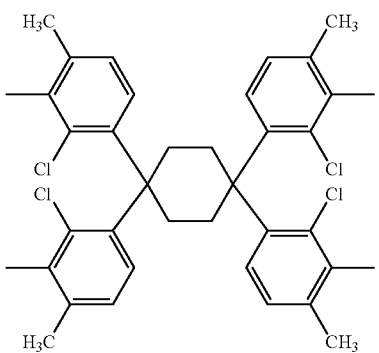
(1-44)
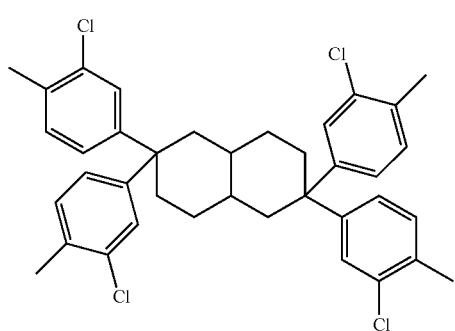
(1-45)
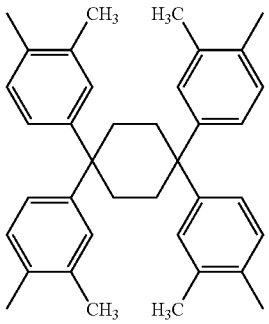

(1-46)
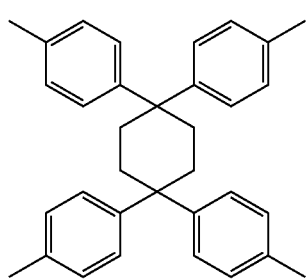
(1-47)
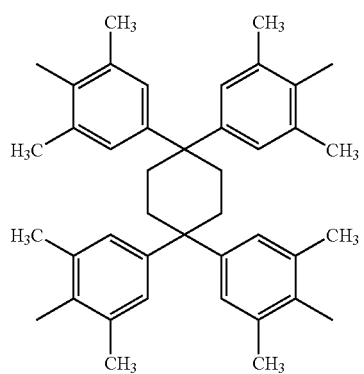
(1-48)
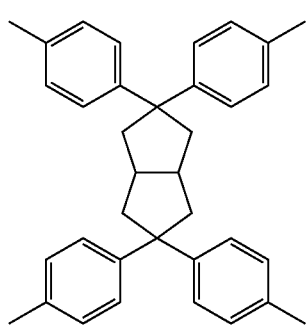
(1-49)
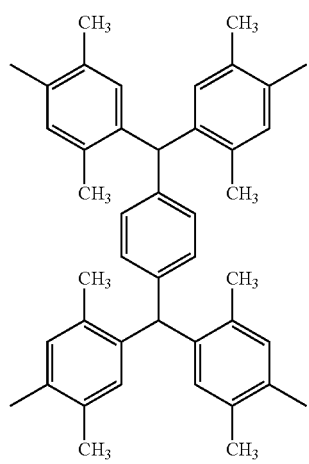
(1-50)
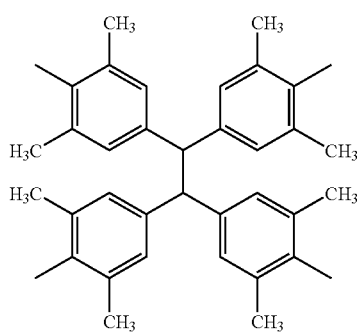
(1-51)
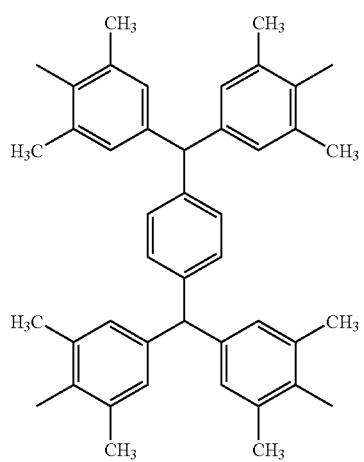
(1-52)
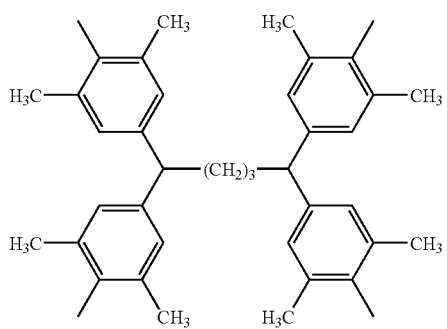
(1-53)
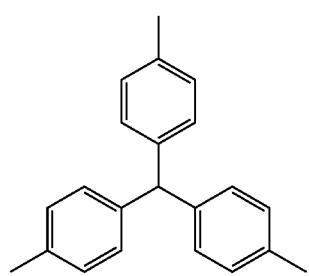

-continued
(1-54)
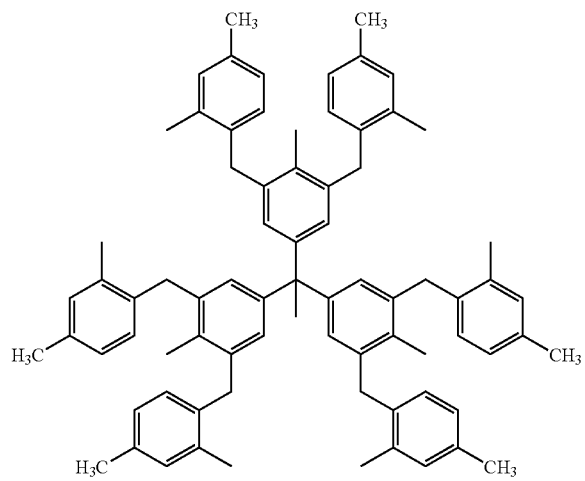
(1-55)
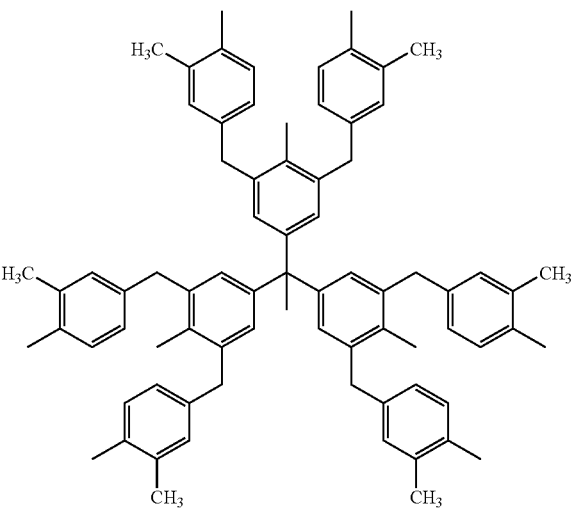
(1-56)
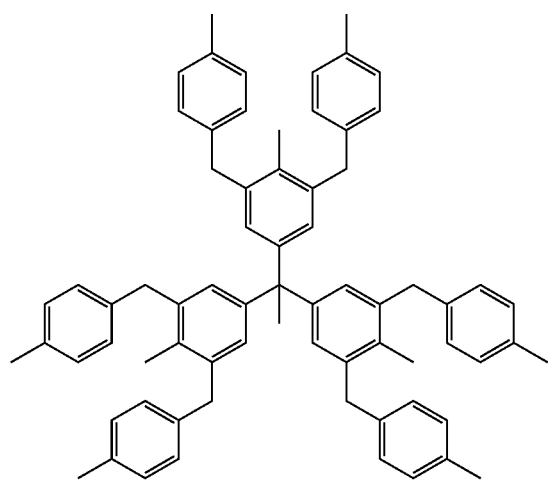
(1-57)
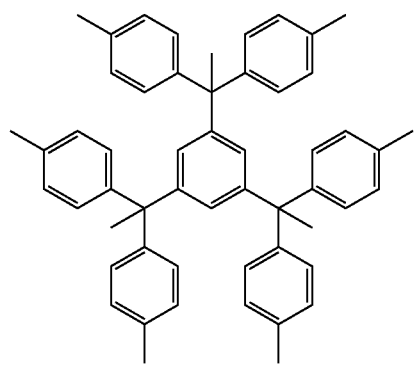
(1-58)
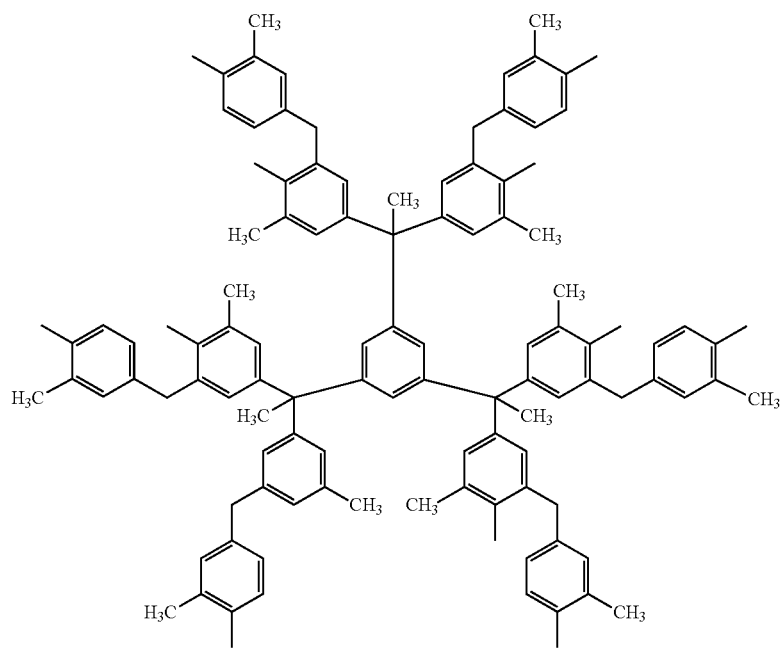

(1-59)
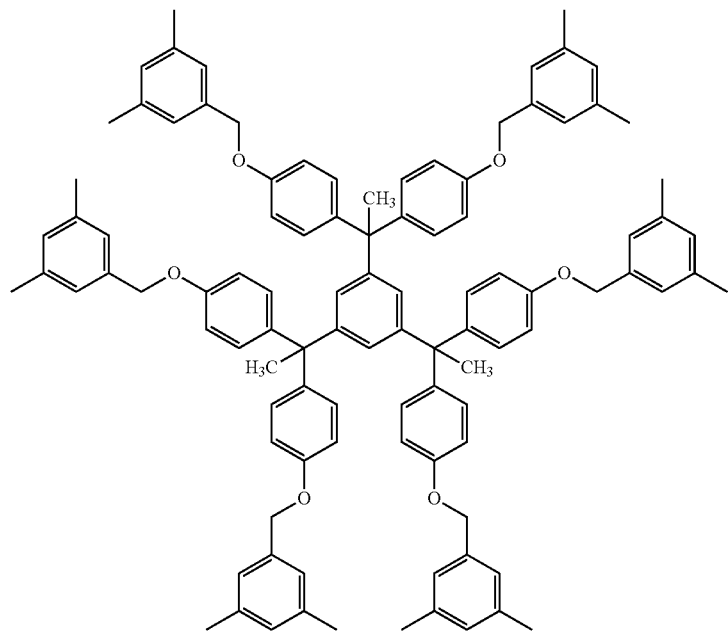
(1-60)
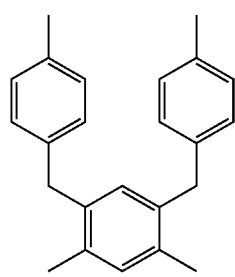
(1-61)
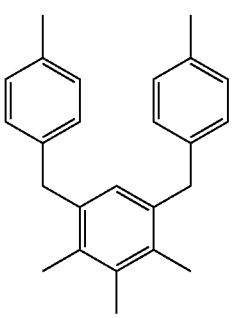
(1-62)
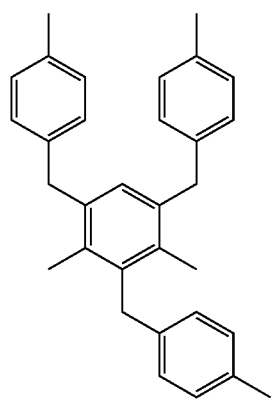
(1-63)
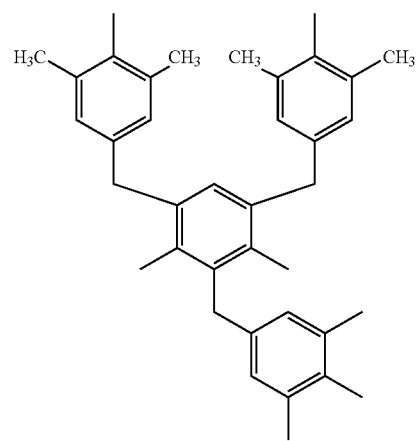

-continued
(1-64)
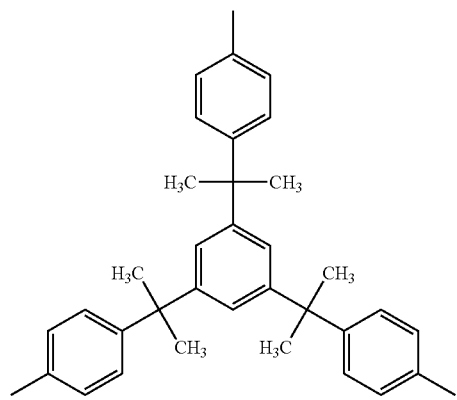
(1-65)
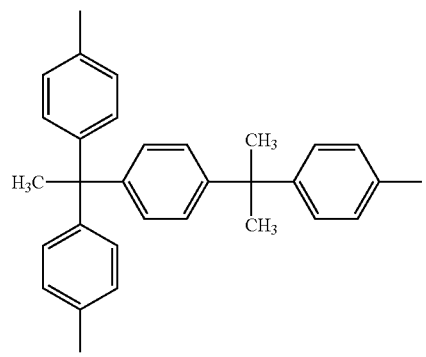
(1-66)
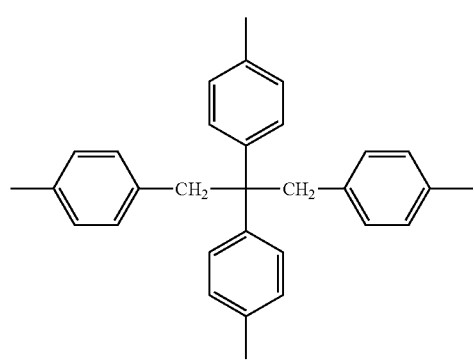
(1-67)
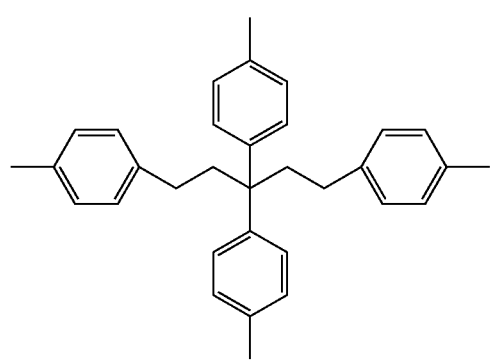
(1-68)
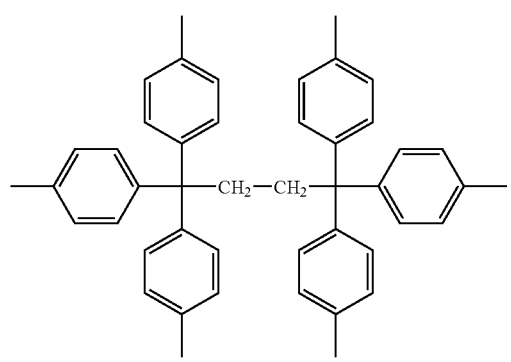
(1-69)
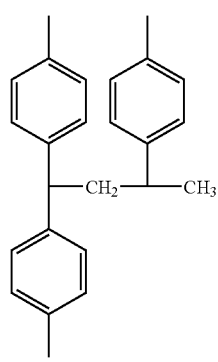
(1-70)
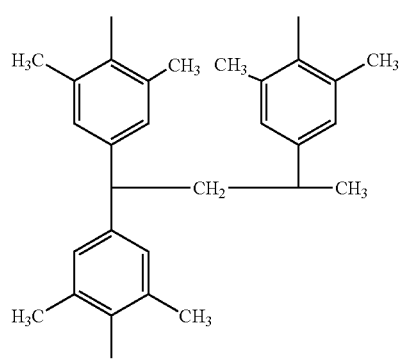
(1-71)
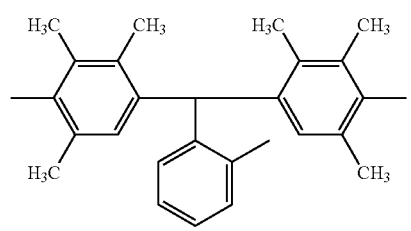

-continued
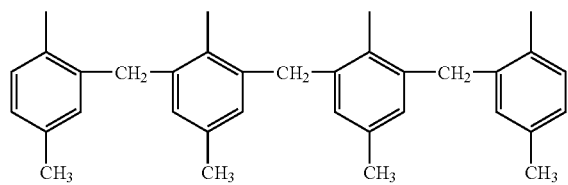
(1-72)
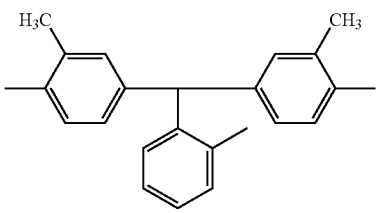
(1-73)
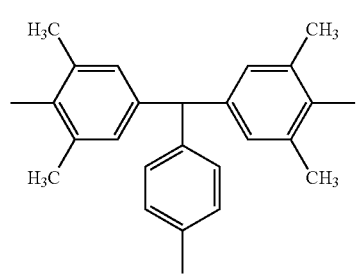
(1-74)
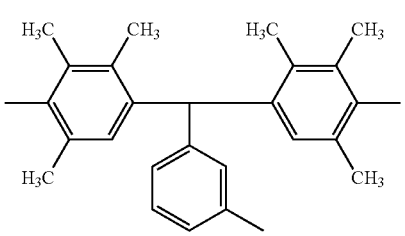
(1-75)
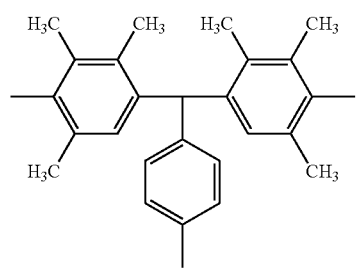
(1-76)
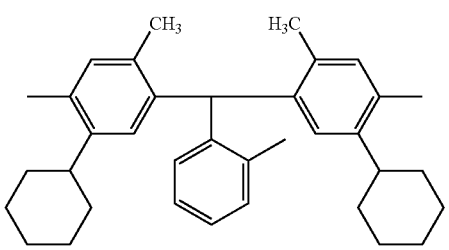
(1-77)
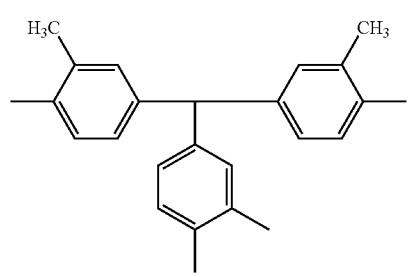
(1-78)
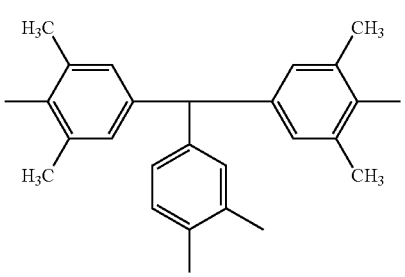
(1-79)
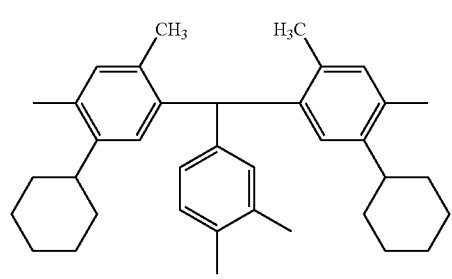
(1-80)
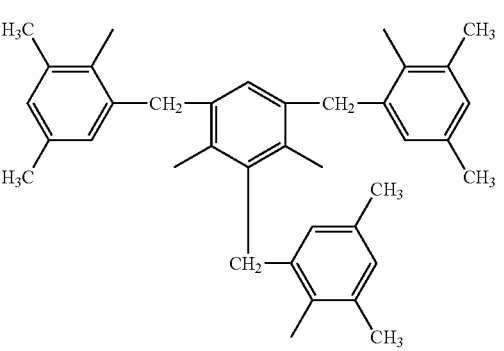
(1-81)

-continued
(1-82)
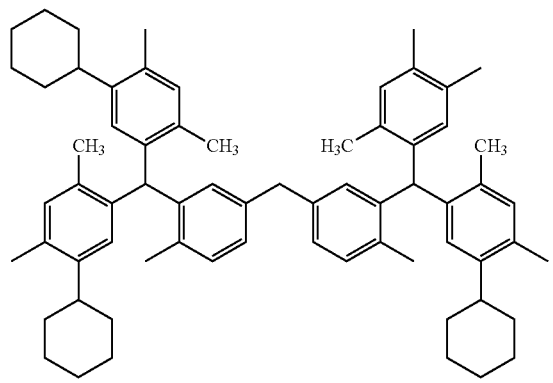
(1-83)
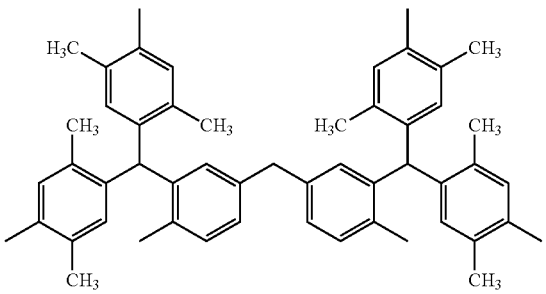
(1-84)
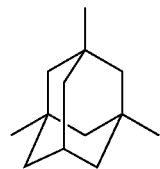
(1-85)
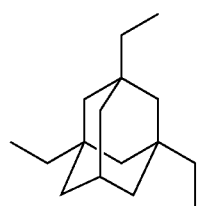
(1-86)
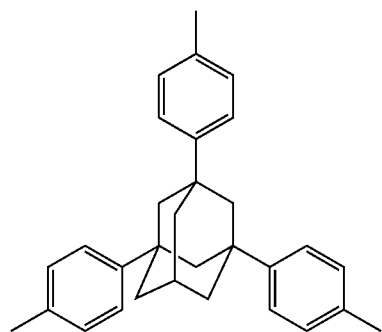
(1-87)
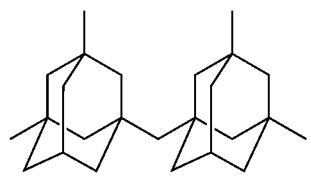
(1-88)
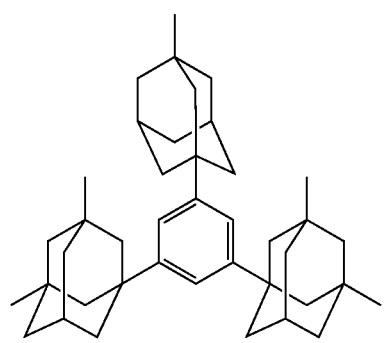
(1-89)
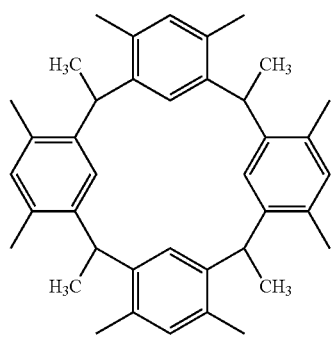
(1-90)
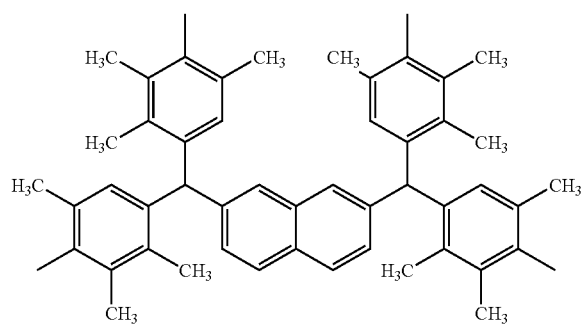
(1-91)
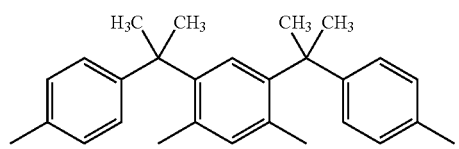

(1-92)

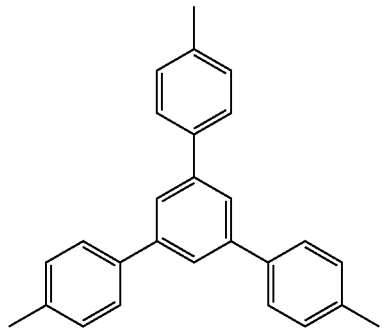

(1-93)

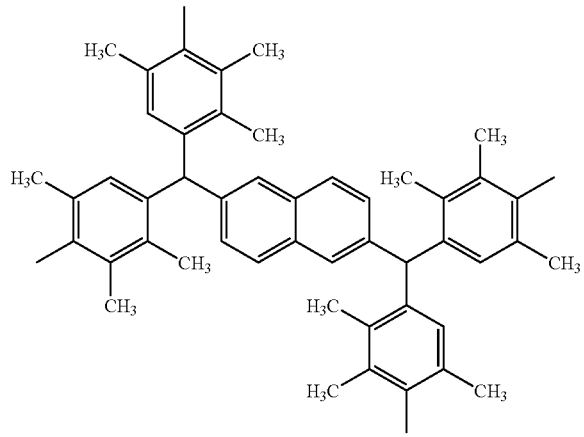

In the formula (1), X represents —O—, —CH$_2$C(=O)—O—, —C(=O)—O—, or —Ar—O—, provided that Ar represents a substituted or unsubstituted 1,4-phenylene group. R$^1$ in the above formula (1) represents an acid-dissociable group which is a substituted or unsubstituted tertiary hydrocarbon group having 4 to 12 carbon atoms or a substituted or unsubstituted acetal group. As specific examples of R$^1$ (acid-dissociable group) in the formula (1), a tertiary hydrocarbon group such as a t-butyl group, a 1-methylcyclopentyl group, 1-ethylcyclopentyl group, a 2-methyl-2-adamantyl group, a 2-ethyl-2-adamantyl group; and an acetal group such as 1-ethoxyethyl group, a tetrahydrofuranyl group, and a tetrahydropyranyl group can be given.

In the formula (1), Y represents a single bond, —R$^2$—, —CH$_2$—C(=O)—O—R$^2$—, —C(=O)—O—R$^2$, or —Ar—O—R$^2$— (wherein R$^2$ represents a substituted or unsubstituted methylene group or a substituted or unsubstituted alkylene group having 2 to 30 carbon atoms and Ar represents a substituted or unsubstituted 1,4-phenylene group). As specific examples of the substituted or unsubstituted alkylene group having 2 to 30 carbon atoms represented by R$^2$ in the formula (1), (1) a substituted or unsubstituted linear or branched alkylene group having 1 to 10 carbon atoms, (2) a substituted or unsubstituted monocyclic alkylene group having 4 to 10 carbon atoms, and (3) a substituted or unsubstituted crosslinked bicyclo, tricyclo, or tetracyclo hydrocarbon group having 4 to 30 carbon atoms can be given.

Specific examples of the substituted or unsubstituted linear or branched alkylene group (1) having 1 to 10 carbon atoms include a methylene group, an ethylene group, 1,3-propylene group, a tetramethylene group, a pentamethylene group, a hexamethylene group, a heptamethylene group, an octamethylene group, a nonamethylene group, a decamethylene group, a 2-methyl-1,3-propylene group, a 2-methyl-1,2-propylene group, and a 2-methyl-1,4-butylene group.

Specific examples of the substituted or unsubstituted monocyclic alkylene group (2) having 4 to 10 carbon atoms include cyclopentylene groups such as a 1,3-cyclopentylene group, cyclohexylene groups such as a 1,4-cyclohexylene group, and cyclooctylene groups such as a 1,5-cyclooctylene group.

Specific examples of the substituted or unsubstituted crosslinked bicyclo, tricyclo, or tetracyclo hydrocarbon group (3) having 4 to 30 carbon atoms include norbornylene groups such as a 1,4-norbornylene group and a 2,5-norbornylene group and admantylene groups such as a 1,3-admantylene group and a 2,6-admantylene group.

Preferable examples of the substituent which may be contained in the above-mentioned groups (1) to (3) include an alkoxy group having 1 to 4 carbon atoms, a halogen group, a cyano group, a hydroxyl group, a carboxy group, an alkoxy carbonyl group, and a nitro group.

In the formula (1), Z represents the organic groups shown by any one of the following formulas (2) to (5). When m is 2 or 3, these organic groups may be either the same or different.

$$—SO_3^-M_1^+ \quad (2)$$

$$—M_2^{+-}O_3S—R^3 \quad (3)$$

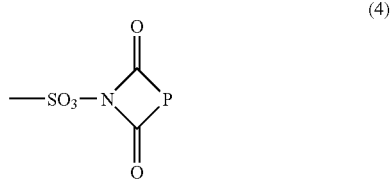
(4)

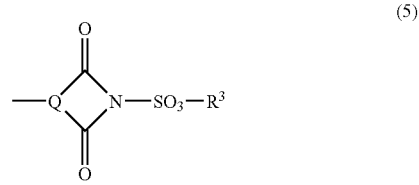
(5)

M$_1^+$ in the formula (2) represents a monovalent onium cation. M$_2^+$ in the formula (3) represents a monovalent onium cation. R$^3$ in the formula (3) and formula (5) represents a substituted or unsubstituted alkyl group or a substituted or unsubstituted aryl group, having 1 to 15 carbon atoms. As specific examples of the substituted or unsubstituted alkyl group having 1 to 15 carbon atoms represented by R$^3$ in the above formulas (3) and (5), a trifluoromethyl group, a nonafluoro-n-butyl group, a perfluoro-n-octyl group, and an n-octyl group can be given. As specific examples of the substituted or unsubstituted aryl group having 1 to 15 carbon atoms represented by R$^3$ in the above formulas (3) and (5), a phenyl group, a 4-methylphenyl group, a 4-trifluoromethylphenyl group, a 2-(bicyclo[2.2.1] heptan-2-yl)-1,1,2,2-tetrafluoroethyl group, and a perfluorophenyl group can be given. P in the formula (4) represents a substituted or unsubstituted alkylene group or a substituted or unsubstituted arylene group, having 2 to 10 carbon atoms.

As specific examples of the monovalent onium cation represented by M⁺ in the formula (2), a sulfonium cation, an iodonium cation, a phosphonium cation, a diazonium cation, an ammonium cation, and a pyridinium cation can be given. Of these, the sulfonium cation shown by the following formula (2a) or the iodonium cation shown by the following formula (2b) are preferable.

In the formula (2a), $R^5$, $R^6$, and $R^7$ individually represent a substituted or unsubstituted alkyl group having 1 to 10 carbon atoms or a substituted or unsubstituted aryl group having 6 to 18 carbon atoms. Two or more of $R^5$, $R^6$, and $R^7$ may bond each other with the sulfur atom in the formula to form a ring.

In the formula (2b), $R^8$ and $R^9$ individually represent a substituted or unsubstituted alkyl group having 1 to 10 carbon atoms or a substituted or unsubstituted aryl group having 6 to 18 carbon atoms. Two or more of $R^8$ and $R^9$ may bond each other with the iodine atom in the formula to form a ring.

As specific examples of the unsubstituted alkyl group having 1 to 10 carbon atoms in the formulas (2a) and (2b), linear or branched alkyl groups such as a methyl group, an ethyl group, an n-propyl group, an i-propyl group, an n-butyl group, a 1-methylpropyl group, a 2-methylpropyl group, a t-butyl group, an n-pentyl group, an i-pentyl group, a 1,1-dimethylpropyl group, a 1-methylbutyl group, an n-hexyl group, an i-hexyl group, a 1,1-dimethylbutyl group, an n-heptyl group, an n-octyl group, an i-octyl group, a 2-ethylhexyl group, an n-nonyl group, and an n-decyl group can be given. As examples of the substituents that may be introduced into the alkyl group, an aryl group having 6 to 30 carbon atoms, a linear, branched, or cyclic alkenyl group having 2 to 30 carbon atoms, and a group having 1 to 30 atoms containing a hetero atom such as a halogen atom, an oxygen atom, a nitrogen atom, a sulfur atom, a phosphorus atom, or a silicon atom can be given.

As specific examples of the substituted linear or branched alkyl group having 1 to 10 carbon atoms in the above formulas (2a) and (2b), a benzyl group, a methoxymethyl group, a methylthiomethyl group, an ethoxymethyl group, an ethylthiomethyl group, a phenoxymethyl group, a methoxycarbonylmethyl group, an ethoxycarbonylmethyl group, an acetylmethyl group, a fluoromethyl group, a trifluoromethyl group, a chloromethyl group, a trichloromethyl group, a 2-fluoropropyl group, a (trifluoroacetyl)methyl group, a (trichloroacetyl) methyl group, a (pentafluorobenzoyl)methyl group, an aminomethyl group, a (cyclohexylamino)methyl group, a (trimethylsilyl)methyl group, a 2-phenylethyl group, a 2-aminoethyl group, and a 3-phenylpropyl group can be given.

As specific examples of the unsubstituted aryl group having 6 to 18 carbon atoms in the above formulas (2a) and (2b), a phenyl group, a 1-naphthyl group, a 2-naphthyl group, a 1-anthryl group, and a 1-phenanthryl group can be given. As examples of the substituents that may be introduced into these aryl groups, a linear, branched, or cyclic alkyl group having 1 to 30 carbon atoms, and a group having 1 to 30 atoms containing a hetero atom such as a halogen atom, an oxygen atom, a nitrogen atom, a sulfur atom, a phosphorus atom, or a silicon atom can be given.

As specific examples of the substituted aryl group having 6 to 18 carbon atoms in the above formula (2a) and (2b), an o-tolyl group, an m-tolyl group, a p-tolyl group, a 4-hydroxyphenyl group, a 4-methoxyphenyl group, a mesityl group, an o-cumenyl group, a 2,3-xylyl group, a 2,4-xylyl group, a 2,5-xylyl group, a 2,6-xylyl group, a 3,4-xylyl group, a 3,5-xylyl group, a 4-fluorophenyl group, a 4-trifluoromethylphenyl group, a 4-chlorophenyl group, a 4-bromophenyl group, and a 4-iodophenyl group can be given. As examples of the ring which can be formed by bonding of the two or more groups together with the sulfur atom or the iodine atom in the above formulas (2a) and (2b), 5 to 7 member rings can be given.

As specific examples of preferable monovalent onium cations, the sulfonium cations shown by the following formulas (2a-1) to (2a-64) and the iodonium cations shown by the following formulas (2b-1) to (2b-39) can be given.

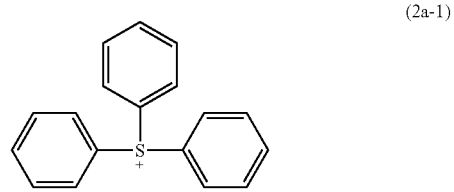

(2a-1)

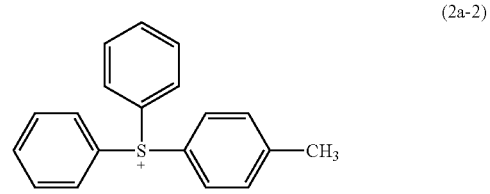

(2a-2)

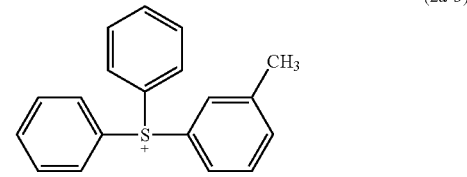

(2a-3)

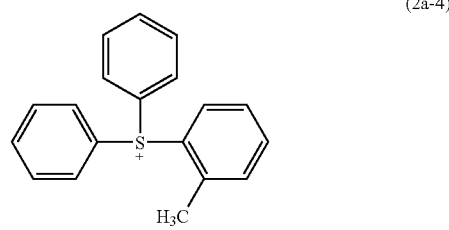

(2a-4)

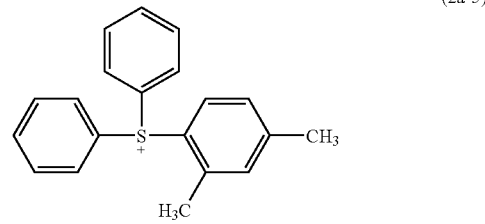

(2a-5)

(2a-6)
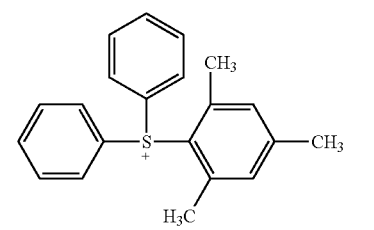
(2a-7)
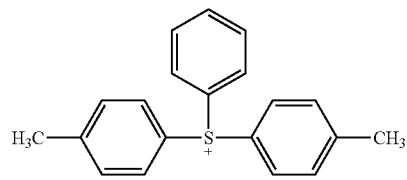
(2a-8)
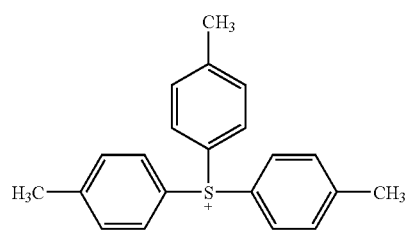
(2a-9)
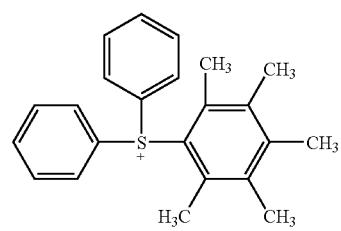
(2a-10)
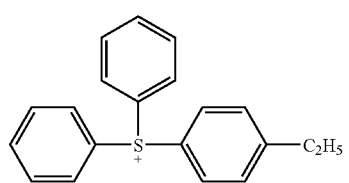
(2a-11)
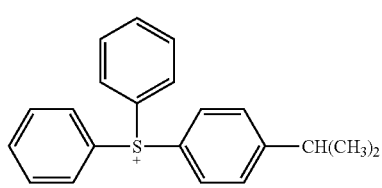
(2a-12)
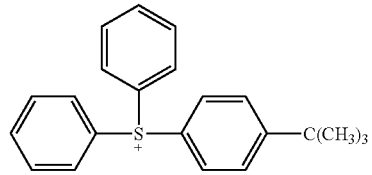
(2a-13)
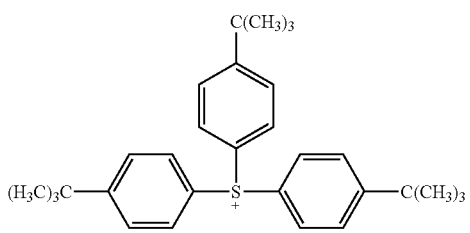
(2a-14)
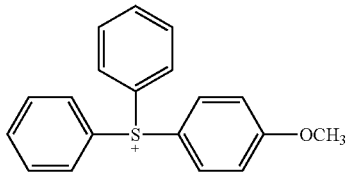
(2a-15)
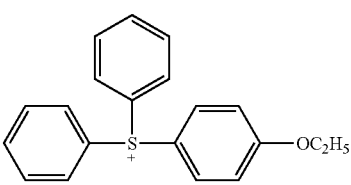
(2a-16)
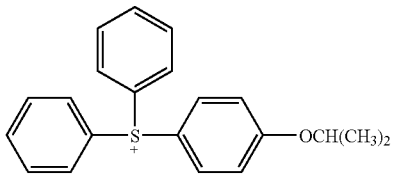
(2a-17)
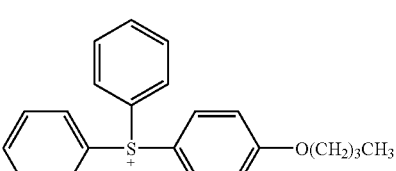
(2a-18)
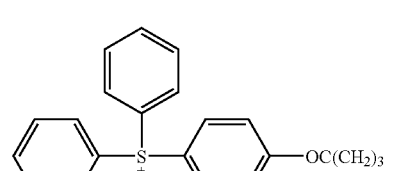
(2a-19)
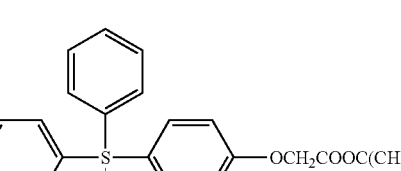
(2a-20)
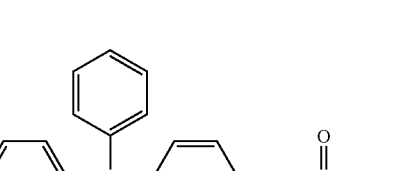

(2a-21)
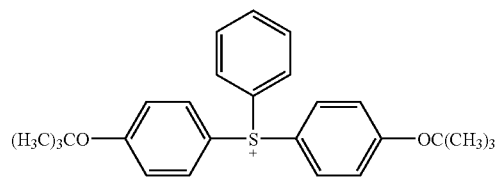
(2a-22)
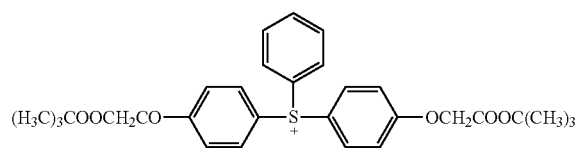
(2a-23)
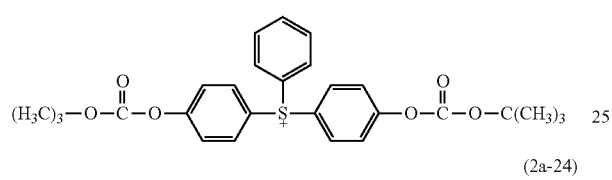
(2a-24)
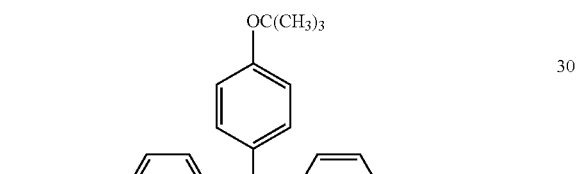
(2a-25)
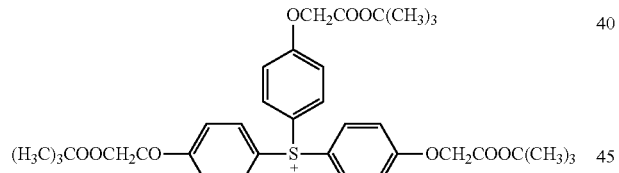
(2a-26)
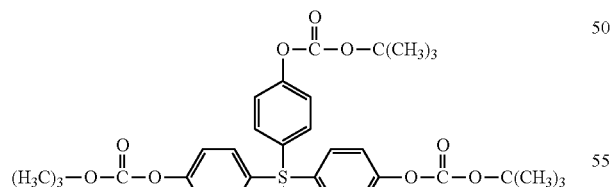
(2a-27)
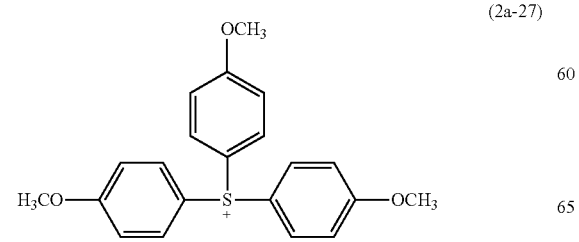
(2a-28)
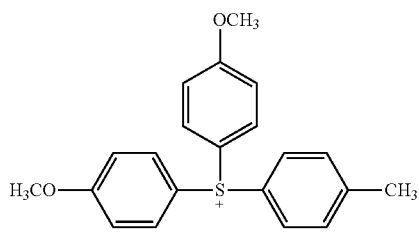
(2a-29)
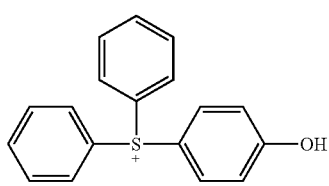
(2a-30)
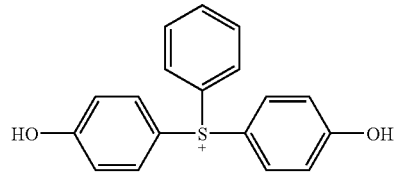
(2a-31)
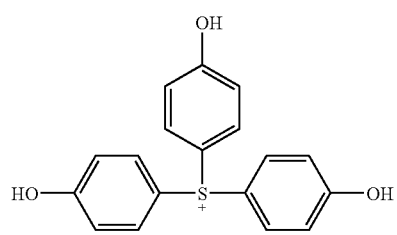
(2a-32)
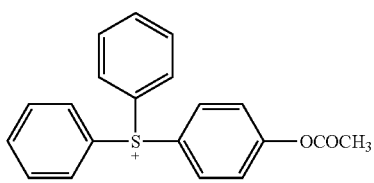
(2a-33)
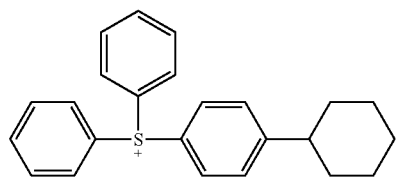
(2a-34)
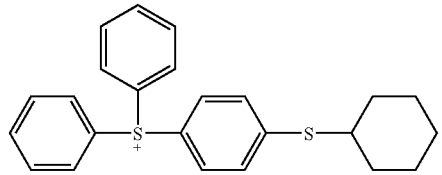

-continued
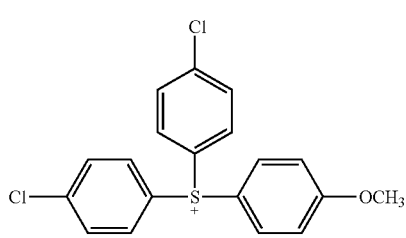
(2a-35)
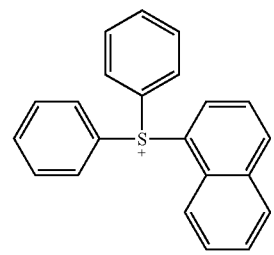
(2a-36)
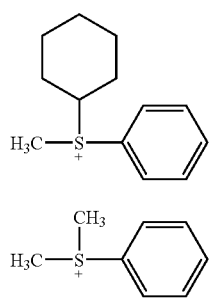
(2a-37)
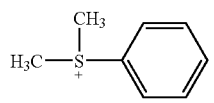
(2a-38)
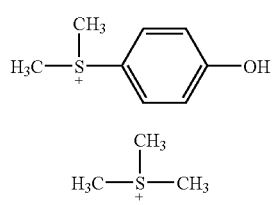
(2a-39)
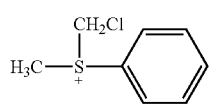
(2a-40)
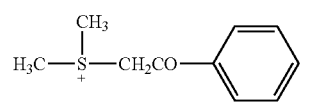
(2a-41)
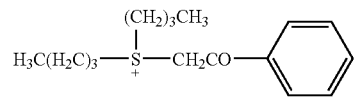
(2a-42)
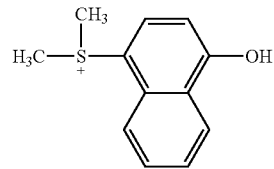
(2a-43)
(2a-44)
-continued
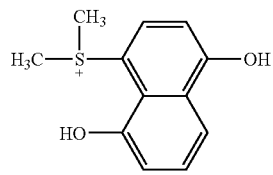
(2a-45)
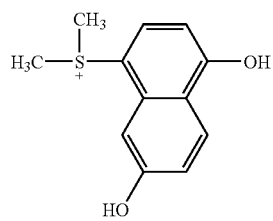
(2a-46)
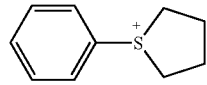
(2a-47)
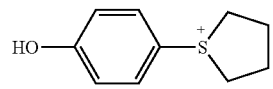
(2a-48)
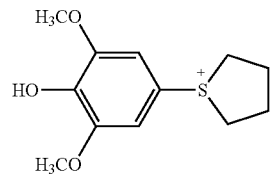
(2a-49)
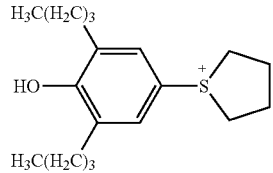
(2a-50)
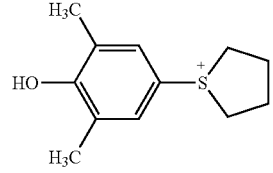
(2a-51)
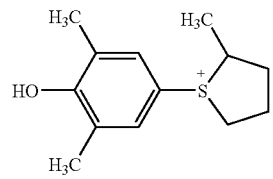
(2a-52)
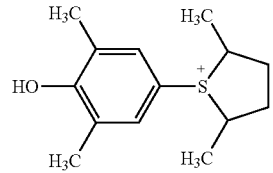
(2a-53)

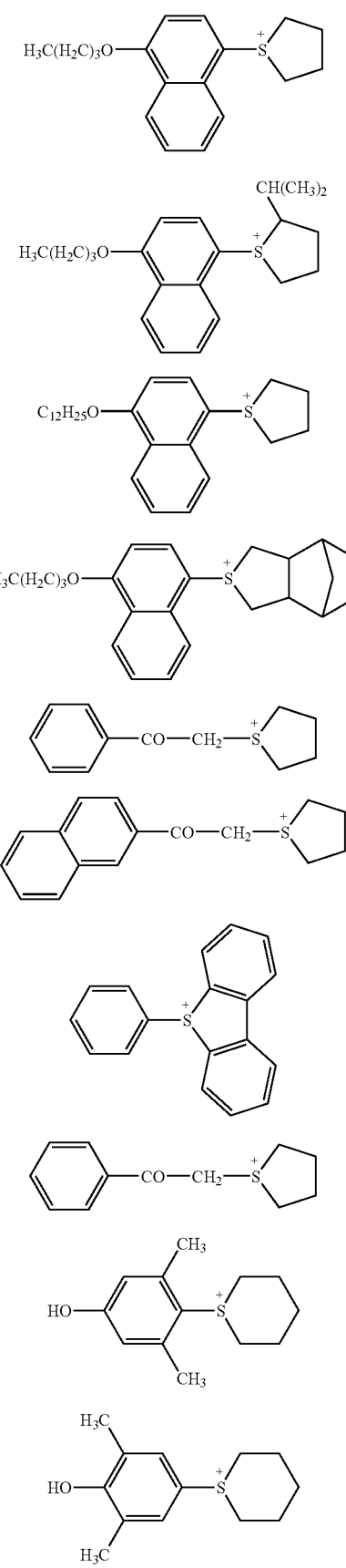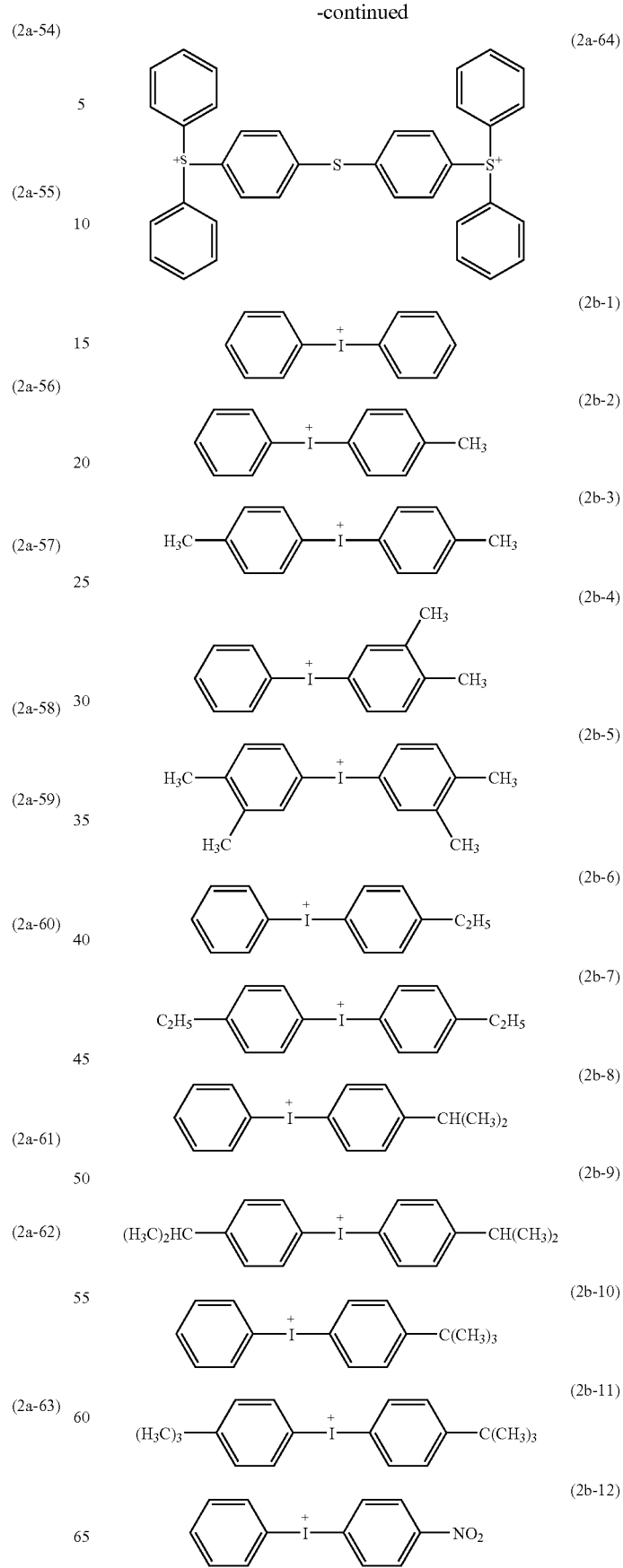

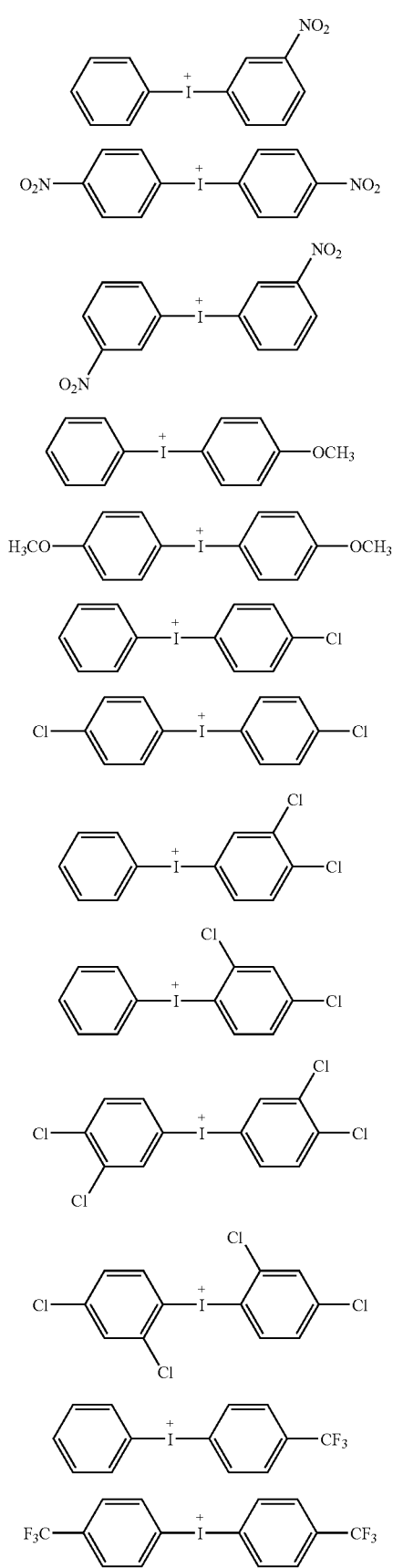
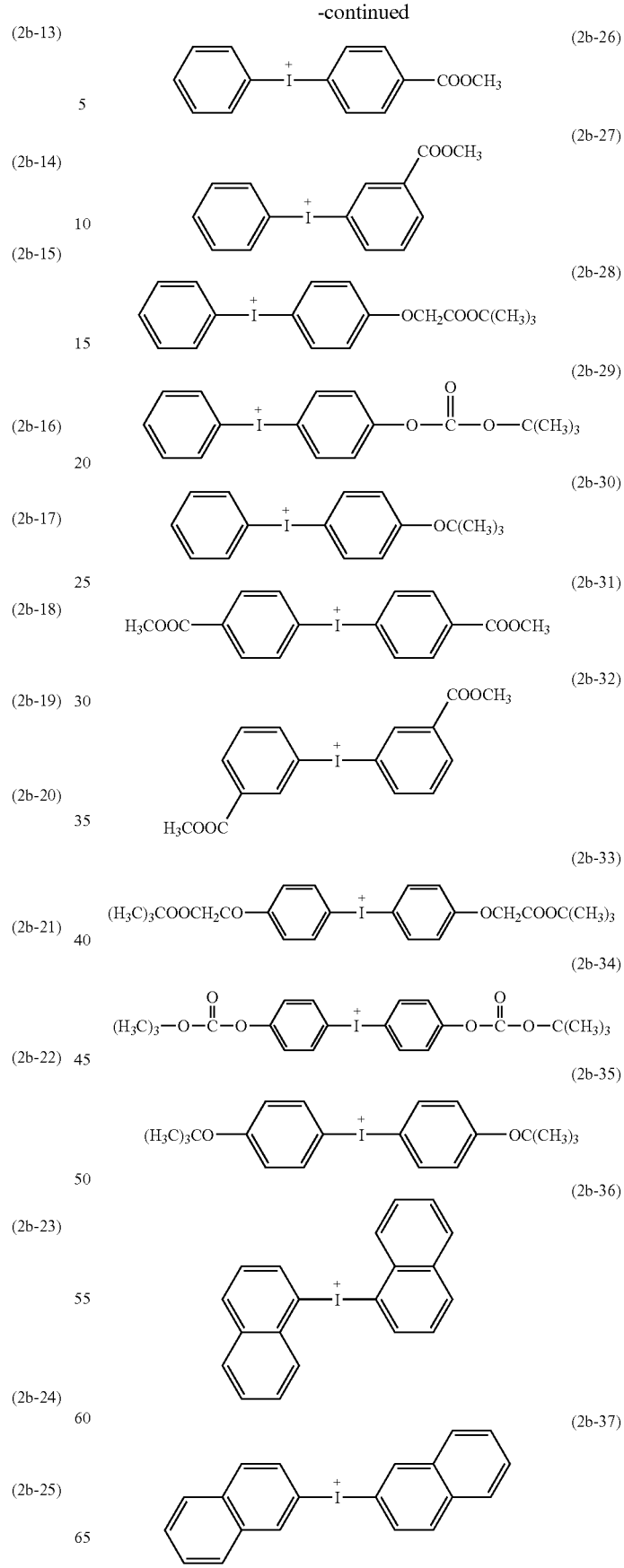

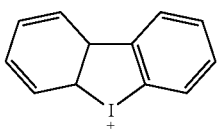
(2b-38)

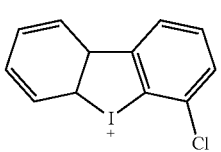
(2b-39)

As specific examples of the monovalent onium cation represented by $M_2^+$ in the formula (3), the groups shown by the following formulas (3-1) to (3-4) can be given.

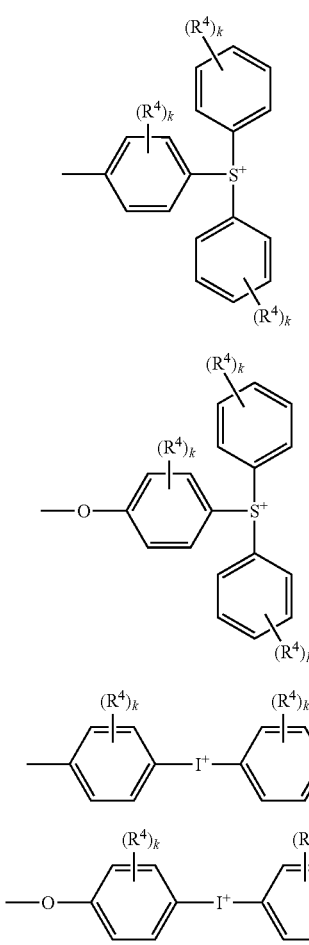

$R^4$ in the formulas (3-1) to (3-4) individually represents an alkyl group, an alkoxyl group, a trifluoromethyl group, or fluorine. As specific examples of the alkyl group, linear or branched alkyl groups having 1 to 8 carbon atoms such as a methyl group, an ethyl group, a propyl group, n-butyl group, a sec-butyl group, a t-butyl group, a hexyl group, and an octyl group; and cycloalkyl groups having 3 to 8 carbon atoms such as a cyclopropyl group, a cyclopentyl group, and a cyclohexyl group can be given. As specific examples of the alkoxy group, linear or branched alkoxy groups having 1 to 8 carbon atoms such as a methoxy group, an ethoxy group, a propoxy group, an n-butoxy group, an iso-butoxy group, a sec-butoxy group, a hexyloxy group, and an octyloxy group can be given. k in the formulas (3-1) to (3-4) individually shows an integer of 0 to 3.

As examples of the alkylene group having 2 to 10 carbon atoms and the arylene group represented by P in the formula (4), the groups shown by the following formulas (4-1) to (4-4) can be given.

(4-1)

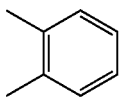
(4-2)

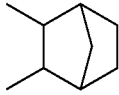
(4-3)

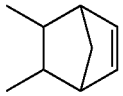
(4-4)

Q in the above formula (5) represents a group shown by any one of the following formulas (6) to (8).

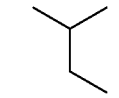
(6)

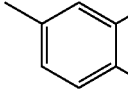
(7)

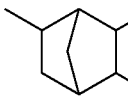
(8)

(Process for Producing Low-Molecular-Weight Compound)
The low-molecular-weight compound contained in the radiation-sensitive composition of the present invention can be produced by any of the following processes (1) to (3).
Process 1: A process of condensing a compound having at least one of a phenolic hydroxyl group and a carboxyl group with an onium salt by etherification or esterification in the presence of at least one selected from the group consisting of an acid, a base, and a dehydrating agent.
Process (2): A process of reacting a compound having a halogenated sulfonyl group and at least one of a phenolic hydroxyl group and a carboxyl group with an N-hydroxydicarboxylmide compound in the presence of a base.
Process (3): A process of reacting a compound having an N-hydroxydicarboxylmide group and at least of a phenolic hydroxyl group and a carboxyl group with a halogenated sulfonyl group in the presence of a base.
According to the process (1), compounds in which Z in the formula (1) is a group shown by the above formula (2) or (3) can be produced. According to the process (2), compounds in which Z in the formula (1) is a group shown by the above formula (4) can be produced. According to the process (3), compounds in which Z in the formula (1) is a group shown by the above formula (5) can be produced.

((B) Solvent)

Specific examples of the solvent (B) contained in the radiation-sensitive composition of the present invention include ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; propylene glycol monoalkyl ethers such as propylene glycol monomethyl ether, propylene glycol monethyl ether, propylene glycol mono-n-propyl ether, and propylene glycol mono-n-butyl ether; propylene glycol dialkyl ethers such as propylene glycol dimethyl ether, propylene glycol diethyl ether, propylene glycol di-n-propyl ether, and propylene glycol di-n-butyl ether; propylene glycol monoalkyl ether acetates such as propylene glycol monomethyl ether acetate, propylene glycol monethyl ether acetate, propylene glycol mono-n-propyl ether acetate, and propylene glycol mono-n-butyl ether acetate; lactic acid esters such as methyl lactate, ethyl lactate, n-propyl lactate, and i-propyl lactate; aliphatic carboxylic acid esters such as n-amyl formate, i-amyl formate, ethyl acetate, n-propyl acetate, i-propyl acetate, n-butyl acetate, i-butyl acetate, n-amyl acetate, i-amyl acetate, i-propyl propionate, n-butyl propionate, and i-butyl propionate; other esters such as ethyl hydroxylacetate, ethyl 2-hydroxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, 3-methoxybutyl acetate, 3-methyl-3-methoxybutyl acetate, 3-methyl-3-methoxybutyl propionate, 3-methyl-3-methoxybutyl butyrate, methyl acetoacetoate, ethyl acetoacetate, methyl pyruvate, and ethyl pyruvate; aromatic hydrocarbons such as toluene and xylene; ketones such as methyl ethyl ketone, methyl propyl ketone, methyl butyl ketone, 2-heptanone, 3-heptanone, 4-heptanone, and cyclohexanone; amides such as N-methylformamide, N,N-dimethylformamide, N-methylacetamide, N,N-dimethylacetamide, and N-methylpyrrolidone; and lactones such as γ-butyrolactone. These solvents (B) may be used individually or in combination of two or more.

(Content of Low-Molecular-Weight Compound (A))

The content of the low-molecular-weight compound (A) in the radiation-sensitive composition of the present invention is preferably 80 mass % or more, and more preferably 90 mass % or more of 100 mass % of the total solid component in the radiation-sensitive composition. If the content of the low-molecular-weight compound (A) is below 80 mass %, a sufficient effect of the present invention may not be obtained and line edge roughness may be impaired. Although there are no specific limitations to the upper limit of the content of the low-molecular-weight compound (A), the content of 100 mass % or less is acceptable.

(Other Components)

Components other than the low-molecular-weight compound (A) and the solvent (B) may be optionally added to the radiation-sensitive composition of the present invention. As examples of the other components which can be added, a radiation-sensitive acid generator, an alkali solubility controller, an acid diffusion controller, an acid-dissociable alkali-soluble resin, a surfactant, and a photosensitizer can be given.

As examples of the radiation-sensitive acid generator, onium salt compounds such as a sulfonyloxyimide compound, a sulfonium salt compound, and an iodonium salt compound; a sulfone compound, a sulfonate compound, a diazonium salt compound, a disulfonylmethane compound, an oxime sulfonate compound, and a hydrazine sulfonate compound can be given. The details of these compounds are described below.

As an example of the sulfonyloxyimide compound, a compound of the following formula (9) can be given:

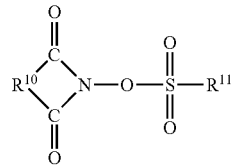

(9)

wherein $R^{10}$ represents a divalent group such as an alkylene group, an arylene group, an alkoxylene group, and $R^{11}$ represents a monovalent group such as an alkyl group, an aryl group, a halogenated alkyl group, and a halogenated aryl group.

Specific examples of the sulfonyloxyimide compound include N-(trifluoromethanesulfonyloxy)bicyclo[2.2.1] hepte-5-en-2,3-dicarboxylmide, N-(trifluoromethanesulfonyloxy)-7-oxabicyclo[2.2.1]hept-5-ene-2,3-dicarboxylmide, N-(trifluoromethanesulfonyloxy)bicyclo[2.2.1] heptan-5,6-oxy-2,3-dicarboxylmide, N-(10-camphorsulfonyloxy)succinimide, N-(10-camphorsulfonyloxy)bicyclo[2.2.1]hept-5-ene-2,3-dicarboxylmide, N-(10-camphorsulfonyloxy)-7-oxabicyclo [2.2.1]hept-5-ene-2,3-dicarboxylmide, N-(10-camphorsulfonyloxy)bicyclo[2.2.1]heptan-5,6-oxy-2,3-dicarboxylmide, N-{(5-methyl-5-carboxymethylbicyclo [2.2.1]heptan-2-yl)sulfonyloxy}succinimide, N-(n-octanesulfonyloxy)-7-oxabicyclo[2.2.1]hept-5-ene-2,3-dicarboxylmide, N-(n-octanesulfonyloxy)bicyclo[2.2.1] heptan-5,6-oxy-2,3-dicarboxylmide, N-(4-toluenesulfonyloxy)succinimide, N-(4-toluenesulfonyloxy)bicyclo[2.2.1] hept-5-ene-2,3-dicarboxylmide, N-(4-toluenesulfonyloxy)-7-oxabicyclo[2.2.1]hept-5-ene-2,3-dicarboxylmide, N-(4-toluenesulfonyloxy)bicyclo[2.2.1]heptan-5,6-oxy-2,3-dicarboxylmide, N-(2-trifluoromethylbenzensulfonyloxy)bicyclo[2.2.1] hept-5-ene-2,3-dicarboxylmide, N-(2-trifluoromethylbenzensulfonyloxy)-7-oxabicyclo[2.2.1]hept-5-en-2,3-dicarboxymide, N-(4-trifluoromethylbenzensulfonyloxy)bicyclo[2.2.1] hept-5-ene-2,3-dicarboxylmide, N-(4-trifluoromethylbenzensulfonyloxy)-7-oxabicyclo[2.2.1]hept-5-en-2,3-dicarboxylmide, N-(perfluorobenzenesulfonyloxy)-7-oxabicyclo[2.2.1] hept-5-ene-2,3-dicarboxylmide, N-(1-naphthalenesulfonyloxy)bicyclo[2.2.1]hept-5-ene-2,3-dicarboxylmide, N-(1-naphthalenesulfonyloxy)-7-oxabicyclo[2.2.1]hept-5-ene-2, 3-dicarboxylmide, N-(nonafluoro-n-butanesulfonyloxy)bicyclo[2.2.1]hept-5-ene-2,3-dicarboxylmide, N-(nonafluoro-n-butanesulfonyloxy)-7-oxabicyclo[2.2.1]hept-5-ene-2,3-dicarboxylmide, and N-(nonafluoro-n-butanesulfonyloxy)bicyclo[2.2.1]heptan-5,6-oxy-2,3-dicarboxylmide.

Among these sulfonyloxyimide compounds, N-(trifluoromethanesulfonyloxy)bicyclo[2.2.1]hept-5-ene-2,3-dicarboxylmide, N-(10-camphorsulfonyloxy)succinimide, N-(4-toluenesulfonyloxy)succinimide, N-(nonafluoro-n-butanesulfonyloxy)bicyclo[2.2.1]hept-5-ene-2,3- dicarboxylmide, N-{(5-methyl-5-carboxymethylbicyclo[2.2.1]heptan-2-yl)sulfonyloxy}succinimide and the like are preferable.

Examples of the sulfonium salt compound include triphenylsulfonium trifluoromethanesulfonate, triphenylsulfonium nonafluoro-n-butanesulfonate, triphenylsulfonium 2-(bicyclo[2.2.1]heptan-2-yl)-1,1,2,2-tetrafluoroethanesulfonate, triphenylsulfonium 4-toluenesulfonate, triphenylsulfonium 10-camphorsulfonate, triphenylsulfonium n-octanesulfonate, triphenylsulfonium 4-trifluoromethylbenzensulfonate, triphenylsulfonium naphthalenesulfonate, (4-t-butylphenyl)diphenylsulfonium trifluoromethanesulfonate, (4-t-butylphenyl)diphenylsulfonium nonafluoro-n-butanesulfonate, (4-t-butylphenyl)diphenylsulfonium perfluoro-n-octanesulfonate, (4-t-butoxyphenyl)diphenylsulfonium trifluoromethanesulfonate, (4-t-butoxyphenyl)diphenylsulfonium nonafluoro-n-butanesulfonate, (4-t-butoxyphenyl)diphenylsulfonium perfluoro-n-octanesulfonate, (4-hydroxyphenyl)diphenylsulfonium trifluoromethanesulfonate, (4-hydroxyphenyl)diphenylsulfonium nonafluoro-n-butanesulfonate, (4-hydroxyphenyl)diphenylsulfonium perfluoro-n-octanesulfonate, (4-hydroxyphenyl)diphenylsulfonium 10-camphorsulfonate, (4-hydroxyphenyl)diphenylsulfonium n-octanesulfonate, (4-hydroxyphenyl)diphenylsulfonium 2-trifluoromethylbenzensulfonate, (4-hydroxyphenyl)diphenylsulfonium 4-trifluoromethylbenzensulfonate, (4-fluorophenyl)diphenylsulfonium trifluoromethanesulfonate, (4-fluorophenyl)diphenylsulfonium nonafluoro-n-butanesulfonate, (4-fluorophenyl)diphenylsulfonium 10-camphorsulfonate, tris(4-fluorophenyl)sulfonium trifluoromethanesulfonate, tris(4-fluorophenyl)sulfonium nonafluoro-n-butanesulfonate, tris(4-fluorophenyl)sulfonium 10-camphorsulfonate, tris(4-fluorophenyl)sulfonium 4-toluenesulfonate, 2,4,6-trimethylphenyldiphenylsulfonium trifluoromethanesulfonate, 2,4,6-trimethylphenyl diphenylsulfonium 2,4-difluorobenzenesulfonate, and 2,4,6-trimethylphenyl diphenylsulfonium 4-trifluoromethylbenzensulfonate.

Among these sulfonium salt compounds, triphenylsulfonium trifluoromethanesulfonate, (4-hydroxyphenyl)diphenylsulfonium trifluoromethanesulfonate, 2,4,6-trimethylphenyldiphenylsulfonium 4-trifluoromethylbenzensulfonate, and the like are preferable.

Examples of the iodonium salt compound include diphenyliodonium trifluoromethanesulfonate, diphenyliodonium nonafluoro-n-butanesulfonate, diphenyliodonium perfluoro-n-octanesulfonate, diphenyliodonium 4-toluenesulfonate, diphenyliodonium benzenesulfonate, diphenyliodonium 10-camphorsulfonate, diphenyliodonium n-octanesulfonate, diphenyliodonium 2-trifluoromethylbenzensulfonate, diphenyliodonium 4-trifluoromethylbenzensulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, (4-nitrophenyl)phenyliodonium trifluoromethanesulfonate, (4-nitrophenyl)phenyliodonium nonafluoro-n-butanesulfonate, (4-nitrophenyl)phenyliodonium perfluoro-n-octanesulfonate, (4-methoxyphenyl)phenyliodonium trifluoromethanesulfonate, (4-methoxyphenyl)phenyliodonium nonafluoro-n-butanesulfonate, (4-methoxyphenyl)phenyliodonium perfluoro-n-octanesulfonate, (4-fluorophenyl)phenyliodonium trifluoromethanesulfonate, (4-fluorophenyl)phenyliodonium nonafluoro-n-butanesulfonate, (4-fluorophenyl)phenyliodonium 10-camphorsulfonate, bis(4-fluorophenyl)iodonium trifluoromethanesulfonate, bis(4-fluorophenyl)iodonium nonafluoro-n-butanesulfonate, bis(4-fluorophenyl)iodonium 10-camphorsulfonate, bis(4-chlorophenyl)iodonium trifluoromethanesulfonate, bis(4-chlorophenyl)iodonium nonafluoro-n-butanesulfonate, bis(4-chlorophenyl)iodonium perfluoro-n-octanesulfonate, bis(4-chlorophenyl)iodonium n-dodecylbenzenesulfonate, bis(4-chlorophenyl)iodonium 4-toluenesulfonate, bis(4-chlorophenyl)iodonium benzenesulfonate, bis(4-chlorophenyl)iodonium 10-camphorsulfonate, bis(4-chlorophenyl)iodonium n-octanesulfonate, bis(4-chlorophenyl)iodonium 4-trifluoromethylbenzensulfonate, bis(4-trifluoromethylphenyl)iodonium trifluoromethanesulfonate, bis(4-trifluoromethylphenyl)iodonium nonafluoro-n-butanesulfonate, bis(4-trifluoromethylphenyl)iodonium perfluoro-n-octanesulfonate, bis(4-trifluoromethylphenyl)iodonium n-dodecylbenzenesulfonate, bis(4-trifluoromethylphenyl)iodonium 4-toluenesulfonate, bis(4-trifluoromethylphenyl)iodonium 10-camphorsulfonate, bis(4-trifluoromethylphenyl)iodonium n-octanesulfonate, bis(4-trifluoromethylphenyl)iodonium 4-trifluoromethylbenzensulfonate, and bis(4-trifluoromethylphenyl)iodonium perfluorobenzenesulfonate.

Among these iodonium salt compounds, diphenyliodonium trifluoromethanesulfonate, (4-nitrophenyl)phenyliodonium trifluoromethanesulfonate, bis(4-trifluoromethylphenyl)iodonium trifluoromethanesulfonate, bis(4-trifluoromethylphenyl)iodonium nonafluoro-n-butanesulfonate, and bis(4-trifluoromethylphenyl)iodonium perfluoro-n-octanesulfonate are preferable.

As examples of the diazonium salt compound, a disulfonyldiazomethane compound shown by the following formula (10) can be given:

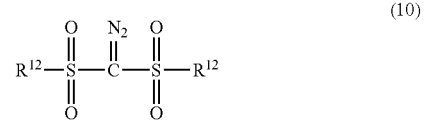

(10)

wherein $R^{12}$ individually represents a monovalent group such as an alkyl group, an aryl group, a halogenated alkyl group, or a halogenated aryl group.

Specific examples of the disulfonyldiazomethane compound include bis(trifluoromethanesulfonyl)diazomethane, bis(cyclohexanesulfonyl)diazomethane, bis(phenylsulfonyl)diazomethane, bis(4-t-butylphenylsulfonyl)diazomethane, bis(4-chlorobenzenesulfonyl)diazomethane, bis(3,3-dimethyl-1,5-dioxaspiro[5.5]dodecane-8-sulfonyl)diazomethane, and bis(1,4-dioxaspiro[4.5]decane-7-sulfonyl)diazomethane. Among these, bis(1,4-dioxaspiro[4.5]decane-7-sulfonyl)diazomethane is preferable.

As examples of the disulfonylmethane compound, compounds shown by the following formula (11) can be given:

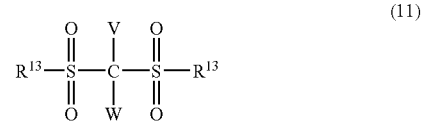

(11)

wherein $R^{13}$ individually represents a linear or branched monovalent aliphatic hydrocarbon group, a cycloalkyl group, an aryl group, an aralkyl group, or a monovalent organic group having a hetero atom, and V and W individually represent an aryl group, a hydrogen atom, a linear or branched monovalent aliphatic hydrocarbon group, or a monovalent organic group having a hetero atom, provided that (i) at least one of V and W is an aryl group, (ii) V and W link to form a monocyclic carbon ring structure or a polycyclic carbon ring structure having at least one unsaturated bond, or (iii) V and W link to form a group shown by the following formula (12),

wherein V' and W' individually represent a hydrogen atom, a halogen atom, a linear or branched alkyl group, a cycloalkyl group, an aryl group, or an aralkyl group, or V' and W', each bonding to the same or different carbon atoms, link to form a monocyclic carbon ring, and r is an integer from 2 to 10.

As examples of the oxime sulfonate compound, compounds of the following formula (13) and (14) can be given:

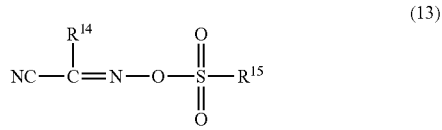

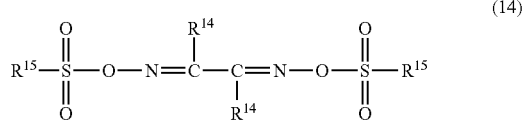

wherein $R^{14}$ and $R^{15}$ individually represent a monovalent organic group. As preferable examples of $R^{14}$ in the formulas (13) and (14), a methyl group, an ethyl group, an n-propyl group, a phenyl group, a tosyl group, a trifluoromethyl group, and a pentafluoroethyl group can be given. As preferable examples of $R^{15}$ in the formulas (13) and (14), a methyl group, a phenyl group, a tosyl group, and a 1-naphthyl group can be given.

Examples of the hydrazinesulfonate compound include bis(benzenesulfonyl)hydrazine, bis(trifluoromethanesulfonyl)hydrazine, bis(pentafluoroethanesulfonyl)hydrazine, trifluoromethanesulfonylhydrazine, pentafluoroethanesulfonylhydrazine, and n-propanesulfonylhydrazine.

The amount of the radiation-sensitive acid generator added is preferably 0.1 to 10 parts by mass, more preferably 1 to 7 parts by mass, and particularly preferably 1 to 5 parts by mass for 100 parts by mass of the low-molecular-weight compound (A). These radiation-sensitive acid generators may be used individually or in combination of two or more.
(Alkali Solubility Controller)

As examples of the alkali solubility controller, a compound obtained by replacing a hydrogen atom of an acidic functional group such as a phenolic hydroxyl group and a carboxyl group with an acid-dissociable group or a t-butoxycarbonylmethyl group can be given. As examples of the acid-dissociable group, a substituted methyl group, a 1-substituted ethyl group, a 1-substituted n-propyl group, a 1-branched alkyl group, a silyl group, a germyl group, an alkoxycarbonyl group, an acyl group, and a cyclic acid-dissociable group can be given.

As the alkali solubility controller, steroids (bile acids) such as cholic acid, deoxycholic acid, and lithocholic acid, compounds containing an alicyclic ring or an aromatic ring such as adamantane carbonic acid or adamantane dicarbonic acid, wherein the hydrogen atom of the carboxyl group in the carbonic acid compound is replaced by the above-mentioned acid-dissociable group or t-butoxycarbonylmethyl group are preferable. These alkali solubility controllers may be used individually or in combination of two or more.

The amount of the alkali solubility controllers added is preferably 0.5 to 10 parts by mass, more preferably 1 to 7 parts by mass, and particularly 1 to 5 parts by mass for 100 parts by mass of the low-molecular-weight compound (A).
(Acid Diffusion Controller)

It is preferable to add to the radiation-sensitive composition of the present invention an acid diffusion controller having an effect of controlling diffusion of an acid generated in the resist coating by irradiation of EB, X-rays, or EUV and to suppress an undesirable reaction in the unirradiated areas. The addition of such an acid diffusion controller improves storage stability of the radiation-sensitive composition. Moreover, the addition of the acid diffusion controller not only increases resolution as a resist, but also can suppress a change in the line width of the resist pattern due to variation of post-exposure delay (PED) from exposure to post-exposure heat treatment, whereby process stability can be remarkably improved.

As the acid diffusion controller, for example, a nitrogen-containing organic compound and a photosensitive basic compound are preferable. As examples of the nitrogen-containing organic compound, compounds shown by the following formula (15) (hereinafter refers to as "nitrogen-containing compounds (α)"), diamino compounds having two nitrogen atoms in the molecule (hereinafter refers to as "nitrogen-containing compounds (β)"), diamino polymers having three or more nitrogen atoms in the molecule (hereinafter refers to as "nitrogen-containing compounds (γ)"), compounds containing an amide group, urea compounds, and heterocyclic compounds containing a nitrogen atom can be given:

wherein $R^{16}$ individually represents a hydrogen atom, an alkyl group, an aryl group, or an aralkyl group. These groups may be substituted by a functional group such as a hydroxyl group, for example.

Examples of the nitrogen-containing compound (α) include monoalkyl amines such as n-hexyl amine, n-heptyl amine, n-octyl amine, n-nonyl amine, and n-decyl amine; dialkylamines such as di-n-butylamine, di-n-pentylamine, di-n-hexylamine, di-n-heptylamine, di-n-octylamine, di-n-nonylamine, and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, and tri-n-decylamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Examples of the nitrogen-containing compound (β) include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenylether, 4,4'-diaminobenzophenone, 4,4'-diaminodiphenylamine, 2,2'-bis (4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene. Examples of the nitrogen-containing compound (γ) include polymers of polyethyleneimine, polyallylamine, and dimethylaminoethyl acrylamide.

Examples of the amide group-containing compounds include formamide, N-methylformamide, N,N-dimethylformamide, acetamide, N-methylacetamide, N,N-dimethylacetamide, propioneamide, benzamide, pyrrolidone, and N-methylpyrrolidone.

Examples of the urea compound include urea, methylurea, 1,1-dimethylurea, 1,3-dimethylurea, 1,1,3,3-tetramethylurea, 1,3-diphenylurea, and tributylthiourea. Examples of the nitrogen-containing heterocyclic compound include imidazoles such as imidazole, 4-methylimidazole, 4-methyl-2-phenylimidazole, benzimidazole, and 2-phenylbenzimidazole; and pyridines such as pyridine, 2-methylpyridine, 4-methylpyridine, 2-ethylpyridine, 4-ethylpyridine, 2-phenylpyridine, 4-phenylpyridine, N-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, morpholine, 4-methylmorpholine, piperazine, 1,4-dimethylpiperazine, 1,4-diazabicyclo[2.2.2]octane, and phenanthroline.

As the nitrogen-containing organic compound, a nitrogen-containing compound having an acid-dissociable group may be used. Examples of the nitrogen-containing compound having an acid-dissociable group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)dioctylamine, N-(t-butoxycarbonyl)diethanolamine, N-(t-butoxycarbonyl)dicyclohexylamine, N-(t-butoxycarbonyl)diphenylamine, N-t-butoxycarbonyldi-n-octylamine, N-t-butoxycarbonyldi-n-nonylamine, N-t-butoxycarbonyldi-n-decylamine, N-t-butoxycarbonyldicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-pyrrolidinemethanol, (R)-(+)-1-(t-butoxycarbonyl)-2-pyrrolidinemethanol, N-t-butoxycarbonyl-4-hydroxypiperidine, N-t-butoxycarbonylpyrrolidine, N-t-butoxycarbonylpiperazine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,0-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, and N-t-butoxycarbonyl-2-methylbenzimidazole. Among these nitrogen-containing organic compounds, the nitrogen-containing compound (α), the nitrogen-containing compound (β), the nitrogen-containing heterocyclic compounds, and the nitrogen-containing compound having an acid-dissociable group are preferable.

The above-mentioned photosensitive basic compound is a component which is efficiently decomposed into neutral fragments in an exposed area, but remains without being decomposed in an unexposed area. Since such a photosensitive basic compound can effectively utilize an acid generated in an exposed area, the compound can increase the sensitivity as compared with a non-photosensitive basic compound.

There are no specific limitations to the type of the photosensitive basic compound inasmuch as the compound has the above-described properties. The compounds shown by the following formulas (16-1) and (16-2) can be given as preferable examples:

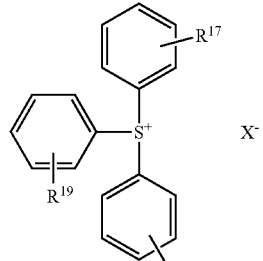

(16-1)

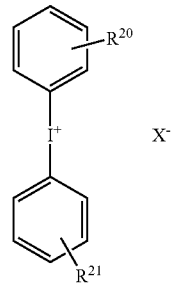

(16-2)

wherein $R^{17}$ to $R^{21}$ individually represent a hydrogen atom, a halogen atom, a substituted or unsubstituted alkyl group having 1 to 10 carbon atoms, or a substituted or unsubstituted alicyclic hydrocarbon group, and $X^-$ represents $OH^-$, $R^{22}OH^-$, or $R^{22}COO^-$, provided that $R^{22}$ is a monovalent organic group.

As the substituted or unsubstituted alkyl group having 1 to 10 carbon atoms shown by $R^{17}$ to $R^{21}$ in the formulas (16-1) and (16-2), a methyl group, an ethyl group, an n-butyl group, a tert-butyl group, a trifluoromethyl group, a fluorine atom, a methoxy group, a t-butoxy group, a t-butoxycarbonyl, a methyloxy group, and the like can be given. $R^{17}$ to $R^{21}$ are preferably a hydrogen atom or a tert-butyl group. As examples of the monovalent organic group represented by $R^{22}$, a substituted or unsubstituted alkyl group and a substituted or unsubstituted aryl group can be given.

As preferable examples of $X^-$ in the formulas (16-1) and (16-2), $OH^-$, $CH_3COO^-$, and the groups shown by the following formulas (17-1) to (17-3) can be given.

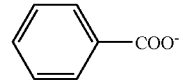

(17-1)

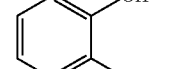

(17-2)

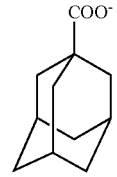

(17-3)

As specific examples of the photosensitive basic compound, a triphenylsulfonium compound shown by the above formula (16-1) in which the anion moiety (X⁻) is OH⁻, CH₃COO⁻, or a group shown by the following formulas (17-2) or (17-3) can be given.

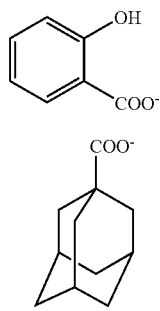

These acid diffusion controllers may be used individually or in combination of two or more. The amount of the acid diffusion controller added is preferably 0.1 to 1 part by mass, and more preferably 0.2 to 0.8 parts by mass for 100 parts by mass of the low-molecular-weight compound (A). If the amount of the acid diffusion controller exceeds 1 part by mass, sensitivity as a resist and developability of the exposed areas tend to decrease. If the amount of the acid diffusion controller is below 0.1 parts by mass, the pattern form and dimensional accuracy as a resist may decrease depending on the process conditions.

Examples of the acid-dissociable alkali-soluble resin include a 4-hydroxystyrene/4-t-butoxystyrene/1-methylcyclopentylacrylate copolymer, 4-hydroxystyrene/4-t-butoxystyrene/1-ethylcyclopentylacrylate copolymer, 4-hydroxystyrene/4-t-butoxystyrene/styrene copolymer, 4-hydroxystyrene/t-butyl acrylate/4-t-butoxystyrene copolymer, 4-hydroxystyrene/4-t-butoxystyrene/2,5-dimethylhexane-2,5-diacrylate copolymer, 4-hydroxystyrene/4-t-butoxystyrene/2,5-dimethylhexane-2,5-diacrylate/styrene copolymer, 4-hydroxystyrene/4-t-butoxystyrene/2-ethyl-2-adamantylacrylate copolymer, 4-hydroxystyrene/4-t-butoxystyrene/1-ethoxyethoxystyrene copolymer, 4-hydroxystyrene/2-methyl-2-adamantylacrylate copolymer, and 4-hydroxystyrene/2-ethyl-2-adamantylacrylate copolymer.

The amount of the acid-dissociable alkali-soluble resin is preferably 0.1 to 10 parts by mass, more preferably 1 to 7 parts by mass, and particularly preferably 1 to 5 parts by mass for 100 parts by mass of the low-molecular-weight compound (A). The above acid-dissociable alkali-soluble resins may be used individually or in combination of two or more.

(Surfactant)

The addition of a surfactant improves coatability of the radiation-sensitive composition, striation, developability as a resist, and the like. Examples of the surfactant include polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate.

The surfactants are available under the trade names of FTOP EF301, FTOP EF303, and ETOP EF352 (manufactured by Tohkem Products Corporation), MEGAFAC F171 and MEGAFAC F173 (manufactured by Dainippon Ink and Chemicals, Inc.), Fluorad FC430 and Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, and Surflon SC-106 (manufactured by Asahi Glass Co., Ltd.), KP 341 (manufactured by Shin-Etsu Chemical Co., Ltd.), Polyflow No. 75 and Polyflow No. 95 (manufactured by Kyoeisha Chemical Co., Ltd.), and the like. These surfactants may be used individually or in combination of two or more. The surfactants are preferably used in an amount of 2 parts by mass or less for 100 parts by mass of the low-molecular-weight compound (A).

(Photo Sensitizer)

As examples of preferable photosensitizer, carbazoles, benzophenones, rose bengals, and anthracenes can be given. These photosensitizers may be used individually or in combination of two or more. The photosensitizers are preferably used in an amount of 10 parts by mass or less for 100 parts by mass of the low-molecular-weight compound (A).

(Preparation of Radiation-Sensitive Composition)

The radiation-sensitive composition of the present invention can be prepared by mixing and dissolving the low-molecular-weight compound (A), the solvent (B), and the optional components according to a general method. In this instance, the components are used in amounts to make the total solid content of the radiation-sensitive composition usually 0.1 to 50 mass %, and preferably 1 to 30 mass %. After dissolving the solid components in the solvent (B), it is desirable to filter the solution through a filter with a pore diameter of about 200 µm, for example.

(Formation of Resist Pattern)

Next, the method of forming a resist pattern using the radiation-sensitive composition of the present invention is described. First, the radiation-sensitive composition prepared in the manner described above is applied to a substrate to form a resist film. As the substrate, a silicon wafer, a wafer covered with aluminum, and the like may be used. As the method of applying the radiation-sensitive composition on the substrate, an application means such as rotation coating, cast coating, and roll coating may be given. In forming the resist film, the coating may be previously treated with heat (PB) at about 70 to 160° C.

Then, the resist film is selectively exposed to radiation (preferably EB) to draw a desired pattern. The drawing conditions are appropriately selected according to the formulation of the radiation-sensitive composition, the type of additives, and the like. In order to stably form a highly accurate fine pattern, the resist film is treated with heat after exposure to radiation (PEB) at a temperature of 50 to 200° C., and preferably 70 to 160° C. If the PEB temperature is below 50° C., sensitivity variation may be broadened in some types of substrate.

After PEB, the resist film is developed using an alkaline developing solution at a temperature of usually 10 to 50° C. for 10 to 200 seconds, and preferably 15 to 30° C. for 15 to 100 seconds, whereby a resist pattern is formed. As the alkaline developing solution, an alkaline aqueous solution prepared by dissolving an alkali compound such as an alkali metal hydroxide, aqueous ammonia, mono-, di-, or tri-alkylamine, mono-, di-, or tri-alkanolamine, heterocyclic amine, tetraalkylammonium hydroxide, choline, 1,8-diazabicyclo[5.4.0]-7-undecene, or 1,5-diazabicyclo[4.3.0]-5-nonene to a concentration of 1 to 10 mass %, preferably 1 to 5 mass %, and particularly preferably 1 to 3 mass % can be used.

An appropriate amount of an aqueous organic solvent such as methanol and ethanol, and a surfactant can be optionally added to the alkaline developing solution. When forming a resist pattern, a protective film and an antistatic film may be preferably provided on the resist film in order to prevent an adverse effect of basic impurities and the like which are present in the environmental atmosphere and to prevent electrostatic charge in the resist film.

EXAMPLES

The present invention is described in detail below by way of examples. Note that the present invention is not limited to the following examples. "Part(s)" and "%" in the examples and comparative examples are expressed on a mass basis, unless otherwise indicated.

Example 1

Synthesis of Low-Molecular Weight Compound (A-1)

18 g of 1,3,5-tris(4-hydroxyphenyl)benzene was dissolved in 500 ml of tetrahydrofuran. 6 g of potassium t-butoxide was added and the mixture was stirred at room temperature for five minutes. After the addition of 10 g of bromo-t-butylacetate dropwise, the mixture was stirred for six hours while heating at 60° C. After evaporating tetrahydrofuran under reduced-pressure, the reaction product was extracted with 300 ml of dichloromethane, purified using a silica gel column, and dried to obtain 4.6 g of 1-(t-butoxycarbonylmethoxyphenyl)-3,5-di(4-hydroxyphenyl)benzene.

12 g of the obtained 1-(t-butoxycarbonylmethoxyphenyl)-3,5-di(4-hydroxyphenyl)benzene was added to a mixed solution of 200 ml of ethanol and 200 ml of water, and 10 g of sodium hydroxide was slowly added. The mixture was stirred for 24 hours while heating 80° C. A dilute hydrochloric acid was slowly added to make the solution acidic. After evaporation of ethanol under reduced pressure, the residue was extracted with 300 ml of methylene chloride. After evaporating methylene chloride under reduced pressure, the resulting powder was dried to obtain 7 g of a compound (a-1) shown below.

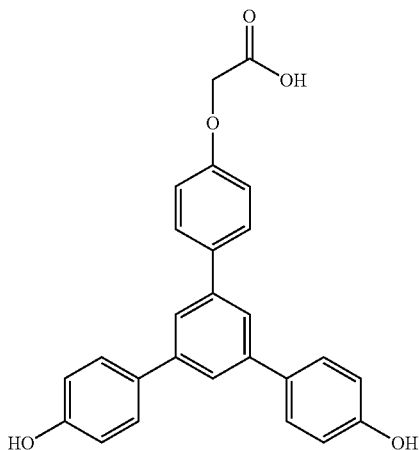

(a-1)

After dissolving 4 g of the obtained compound (a-1) and 1.7 g of 2-iodine ethanol in 100 ml of methylene chloride, 20 g of N,N'-dicyclohexylcarbodiimide was added, and the resulting solution was stirred at room temperature for 24 hours. After the addition of 100 ml of water, the obtained precipitate was removed by filtration. The filtrate was extracted with 100 ml of methylene chloride. The extract was purified using a silica gel column and dried. The purified product was esterified using a generally known dehydration agent to obtain 0.5 g of a compound (a-2) shown below.

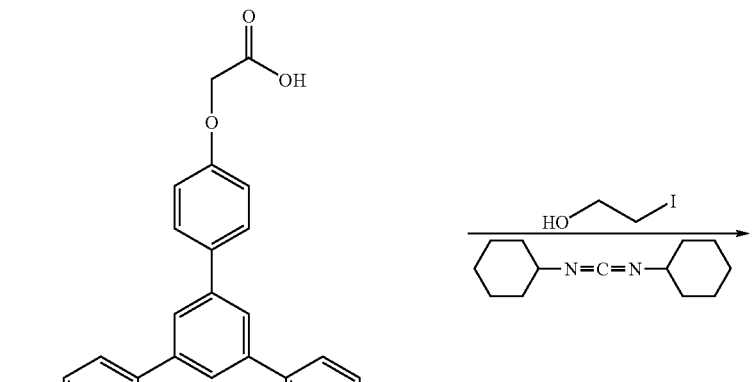

(a-1)

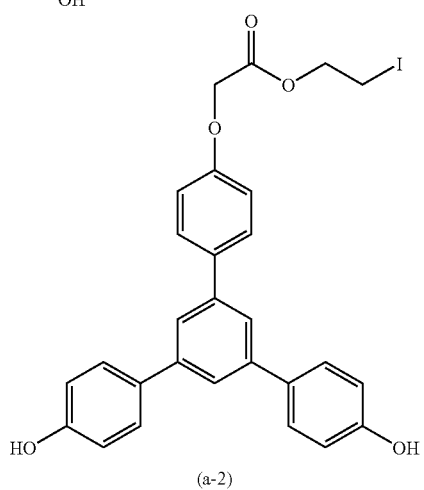

(a-2)

After dissolving 1 g of (4-hydroxyphenyl)diphenylsulfonium trifluoromethanesulfonate in 20 ml of acetone, 0.2 g of sodium hydrogen carbonate was added and the mixture was stirred for one hour. 1.4 g of the compound (a-2) was added and the mixture was stirred at 50° C. for 12 hours. After evaporating acetone under reduced pressure, the residue was extracted with 100 ml of dichloromethane and purified using a silica gel column. The purified product was etherified using a generally known method to obtain 0.2 g of a compound (a-3) shown below.

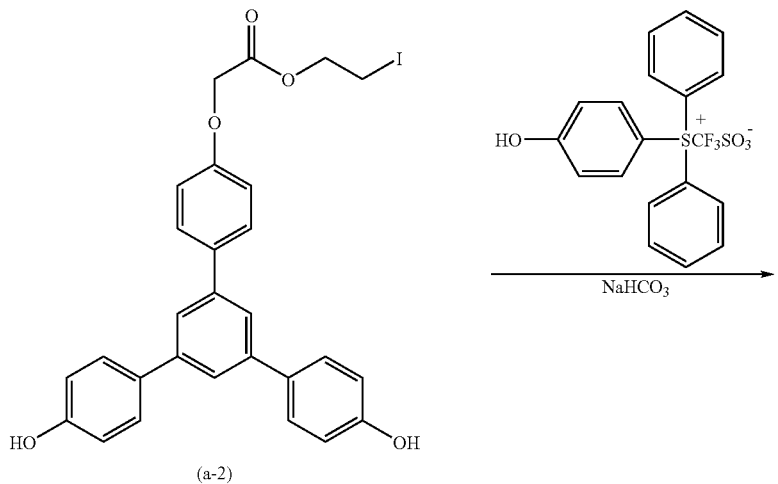

0.4 g of the obtained compound (a-3) was dissolved in 20 ml of tetrahydrofuran. After adding 0.05 g of triethylamine and 0.05 g of 4-dimethylaminopyridine, the resulting mixture was stirred. A solution obtained by dissolving 0.1 g of di-t-butyl-dicarbonate in 5 ml of tetrahydrofuran was slowly added and the mixture was stirred at room temperature for six hours. After evaporating tetrahydrofuran under reduced pressure, the product was extracted with 50 ml of dichloromethane, and purified using a silica gel column to obtain 0.2 g of a compound (A-1) (Example 1) shown below.

(A-1)

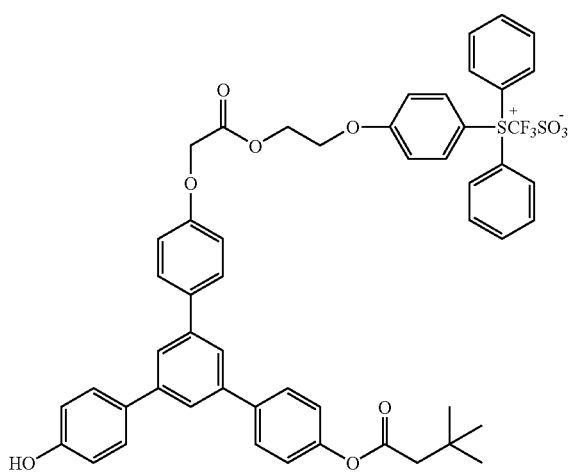

Example 2

Synthesis of Low-Molecular Weight Compound (A-2)

0.1 g of the following compound (A-2) (Example 2) was obtained in the same manner as in Example 1, except for using the following compound (a-4) instead of 1,3,5-tris(4-hydroxyphenyl)benzene.

(a-4)

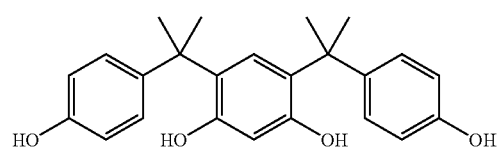

Example 3

Synthesis of Low-Molecular Weight Compound (A-3)

After dissolving 4 g of the compound (a-1) and 5 g of 1,1,2,2-tetrafluoro-5-hydroxypentane-1-sulfonic acid triphenylsulfonium in 100 ml of methylene chloride, 20 g of N,N'-dicyclohexylcarbodiimide was added, and the resulting solution was stirred at room temperature for 24 hours. After the addition of 100 ml of water, the resulting precipitate was removed by filtration. The filtrate was extracted with 100 ml of methylene chloride. The extract product was purified using a silica gel column to obtain 1.1 g of a compound (a-5) shown below.

(a-5)

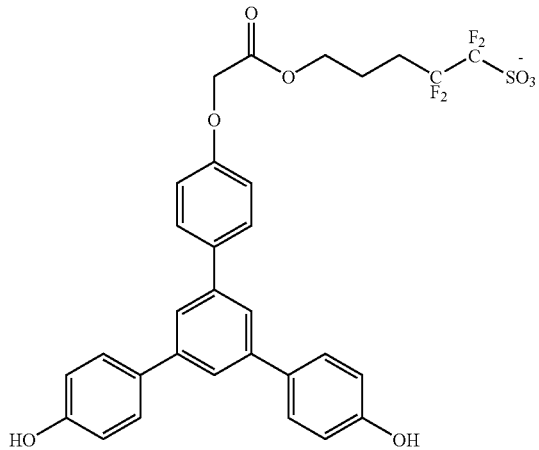

(A-2)

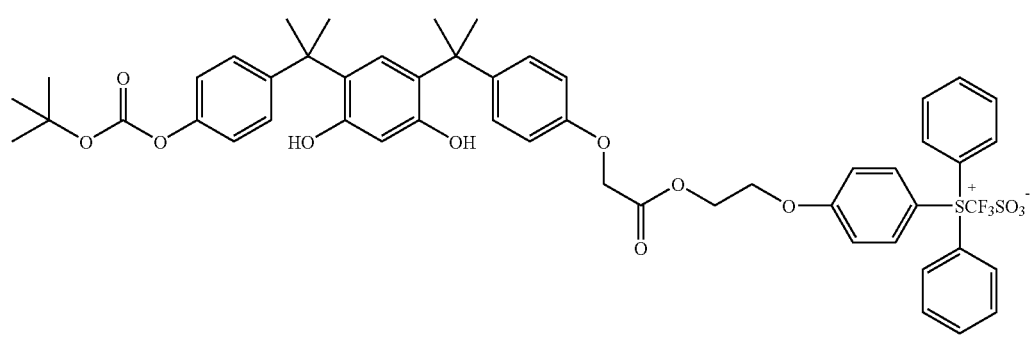

-continued

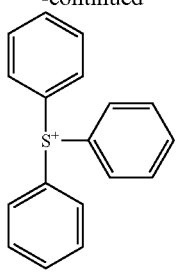

0.1 g of the following compound (A-3) (Example 3) was obtained in the same manner as in Example 1, except for using the compound (a-5) instead of the compound (a-3).

(A-3)

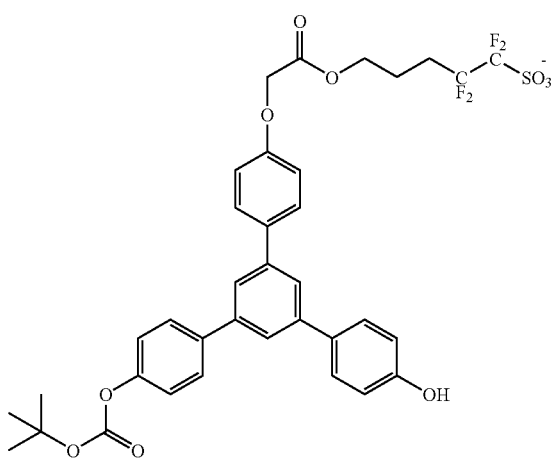

Comparative Example 1

Synthesis of a Low-Molecular Weight Compound (A-4)

3.5 g of 1,3,5-tris(4-hydroxyphenyl)benzene was dissolved in 200 ml of tetrahydrofuran. 1.0 g of triethylamine and 1.2 g of 4-dimethylaminopyridine was further added and the resulting mixture was stirred. A solution obtained by dissolving 2.2 g of di-t-butyl-dicarbonate in 20 ml of tetrahydrofuran was slowly added dropwise and the mixture was stirred at room temperature for six hours. After evaporating tetrahydrofuran under reduced pressure, the product was extracted with 200 ml of dichloromethane, and purified using a silica gel column to obtain 0.7 g of a compound (A-4) (Comparative Example 1) shown below.

(A-4)

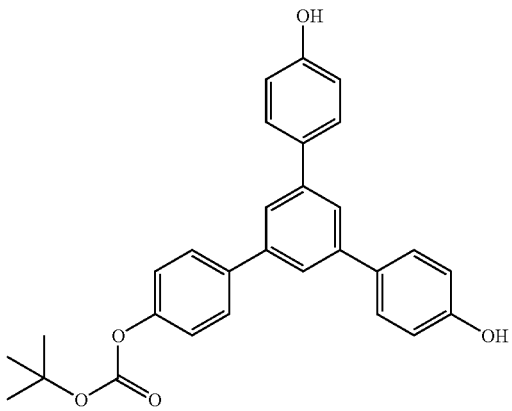

Comparative Example 2

Synthesis of a Low-Molecular Weight Compound (A-5)

3.8 g of the resulting compound (a-4) was dissolved in 200 ml of tetrahydrofuran. After adding 1.0 g of triethylamine and 1.2 g of 4-dimethylaminopyridine, the resulting mixture was stirred. A solution obtained by dissolving 2.2 g of di-t-butyl-dicarbonate in 20 ml of tetrahydrofuran was slowly added dropwise and the mixture was stirred at room temperature for six hours. After evaporating tetrahydrofuran under reduced pressure, the product was extracted with 200 ml of dichloromethane and purified using a silica gel column to obtain 0.2 g of a compound (A-5) (Comparative Example 2) shown below.

(A-5)

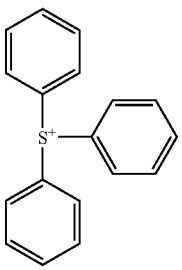

Example 4

A radiation-sensitive composition (Example 4) was prepared by mixing 100 parts of the compound (A-1), 1,200 parts of solvent (B-1), 600 parts of a solvent (B-2), and 0.3 parts of an acid diffusion controller (D-1) to obtain a homogeneous solution, and filtering the solution through a membrane filter with a pore diameter of 200 nm.

Examples 5 to 7 and Comparative Examples 3 and 4

Radiation-sensitive compositions (Examples 5 to 7 and Comparative Examples 3 and 4) were prepared in the same manner as in Example 4, except for using the components of the formulations shown in Table 1. Details of the components (Table 1) used are as follows.
(Solvent (B))
(B-1): Ethyl lactate
(B-2): Propylene glycol monomethyl ether acetate
(Acid Generator (C))
(C-1): Triphenylsulfonium trifluoromethanesulfonate
(Acid Diffusion Controller (D))
(D-1): Tri-n-octylamine

TABLE 1

|  |  | Low-molecular-weight compound (A) | | Solvent (B) | | Acid generator (C) | | Acid diffusion controller (D) | |
| --- | --- | --- | --- | --- | --- | --- | --- | --- | --- |
|  |  | Type | Part | Type | Part | Type | Part | Type | Part |
| Example | 4 | A-1 (Example 1) | 100 | B-1 B-2 | 1200 600 | — | — | D-1 | 0.3 |
|  | 5 | A-1 (Example 1) | 100 | B-1 B-2 | 1200 600 | C-1 | 10 | D-1 | 0.3 |
|  | 6 | A-2 (Example 2) | 100 | B-1 B-2 | 1200 600 | — | — | D-1 | 0.3 |
|  | 7 | A-3 (Example 3) | 100 | B-1 B-2 | 1200 600 | — | — | D-1 | 0.3 |
| Comparative Example | 3 | A-4 (Comparative Example 1) | 100 | B-1 B-2 | 1200 600 | C-1 | 10 | D-1 | 0.3 |
|  | 4 | A-5 (Comparative Example 2) | 100 | B-1 B-2 | 1200 600 | C-1 | 10 | D-1 | 0.3 |

(Evaluation of Radiation-Sensitive Composition)

The following evaluations were carried out using the radiation-sensitive compositions of Examples 4 to 7 and Comparative Examples 3 and 4. The results of the evaluation are shown in Table 2. The evaluation methods were as follows.

[Sensitivity (L/S)]: A resist film with a thickness of 100 nm was prepared by applying the radiation-sensitive composition to a silicon wafer by spin coating using "Clean Track ACT-8" manufactured by Tokyo Electron, Ltd. and heating the coating at 90° C. for 90 seconds (PB, pre-drawing baking). The resist coating produced was irradiated with electron beams using a simplified electron beam drawing device (HL800D manufactured by Hitachi, Ltd., output:50 KeV, current density: 5.0 A/cm$^2$). After PEB (post-baking after drawing) at 90° C. for 90 seconds, the resist was developed by a paddle method using a 2.38 mass % tetramethylammonium hydroxide aqueous solution at 23° C. for one minute, washed with purified water, and dried to form a resist pattern. In this instance, an exposure amount required for forming a 1:1 line-and-space pattern (1L1S) with a line width of 200 nm was regarded as an optimal exposure dose and used as sensitivity (μmC/cm$^2$) for the measurement.

[LWR (line width roughness)]: The line width which was taken as the resolution in the measurement of sensitivity (L/S) was measured at an arbitrarily selected 30 points over a length of 50 μm along the length direction of the line pattern using a scanning electron microscope for semiconductors ("S-9220 high-resolution FEB measuring device", manufactured by Hitachi, Ltd.). The variance of line width variation 3σ (nm) was calculated.

TABLE 2

|  |  | PB temperature ° C./sec | PEB temperature ° C./sec | Sensitivity (μC/cm$^2$) | LWR (nm) |
| --- | --- | --- | --- | --- | --- |
| Example | 4 | 90/90 | 90/90 | 10 | 10 |
|  | 5 | 90/90 | 90/90 | 8 | 10 |
|  | 6 | 90/90 | 90/90 | 10 | 12 |
|  | 7 | 90/90 | 90/90 | 11 | 11 |
| Comparative Example | 3 | 90/90 | 90/90 | 14 | 14 |
|  | 4 | 90/90 | 90/90 | 12 | 15 |

As shown in Table 2, the resists prepared from the radiation-sensitive compositions of Examples 4 to 7 showed sufficiently high sensitivity and good line edge roughness as compared with the those prepared using the radiation-sensitive composition of Comparative Examples 3 and 4.

INDUSTRIAL APPLICABILITY

The radiation-sensitive composition of the present invention is very useful as a chemically-amplified resist for manufacturing semiconductor devices which are anticipated to become more and more micronized. The radiation-sensitive composition of the present invention exhibits excellent sensitivity and controlled film surface roughness in micro-pattern formation using EB, EUV, X-rays, and the like.

The invention claimed is:
1. A radiation-sensitive composition, comprising:
(A) a low-molecular-weight compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, provided that compound (A) is not obtained from chain growth polymerization of a monomer with an unsaturated bond;
(B) a solvent; and
(C) a radiation-sensitive acid-generator other than the low-molecular-weight compound (A),
wherein the content of the low-molecular-weight compound (A) is 80 mass % or more of 100 mass % of the total solid component, and
wherein the low-molecular-weight compound (A) is a compound shown by the following formula (1),

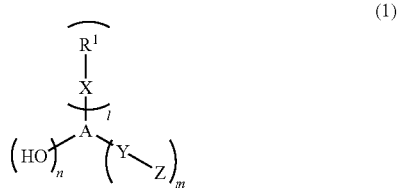

(1)

wherein A represents
(a) an aliphatic group having 1 to 50 carbon atoms,
(b) an aromatic group having 6 to 50 carbon atoms,
(c) an organic group consisting of said aliphatic and said aromatic group, or
(d) a group having a valence which is the sum of l+m+n and which has two or more of the (a), (b) or (c) groups;

X represents —O—, —CH₂C(=O)—O—, —C(=O)—O—, —OC(O)O—, or —Ar¹—O— (wherein Ar¹ represents a 1,4-phenylene group); R¹ represents an acid-dissociable group which is a substituted or unsubstituted tertiary hydrocarbon group having 4 to 12 carbon atoms or a substituted or unsubstituted acetal group; Y represents a single bond, —R²—, —CH₂—C(=O)—O—R²—, —C(=O)—O—R²—, or —Ar²—O—R²— (wherein R² represents a substituted or unsubstituted methylene group or a substituted or unsubstituted alkylene group having 2 to 30 carbon atoms, and Ar² represents a substituted or unsubstituted 1,4-phenylene group); l is an integer from 1 to 4; m is an integer from 1 to 3; n is an integer from 0 to 10; Z is an organic group shown by any one of the following formulas (2) to (5) and, when m is 2 or 3, the organic groups may be either the same or different,

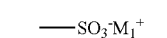     (2)

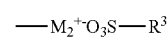     (3)

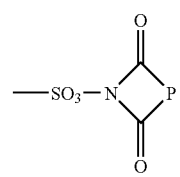     (4)

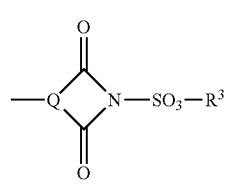     (5)

wherein $M_1^+$ in the formula (2) represents a monovalent onium cation, $M_2^+$ in the formula (3) represents a monovalent onium cation, $R^3$ in the formula (3) and the formula (5) represents a substituted or unsubstituted alkyl group having 1 to 15 carbon atoms or a substituted or unsubstituted aryl group having 1 to 15 carbon atoms, P in the formula (4) represents a substituted or unsubstituted alkylene group having 2 to 10 carbon atoms or a substituted or unsubstituted arylene group having 2 to 10 carbon atoms, and Q in the formula (5) represents a group shown by any one of the following formulas (6) to (8),

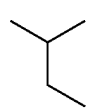     (6)

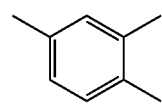     (7)

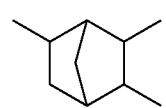     (8)

wherein the low-molecular-weight compound (A) is obtained by reacting a compound having a halogenated sulfonyl group and at least one of a phenolic hydroxyl group and a carboxyl group with an N-hydroxydicarboxylmide compound in the presence of a base.

2. The radiation-sensitive composition according to claim 1, further comprising an acid diffusion controller selected from the group consisting of

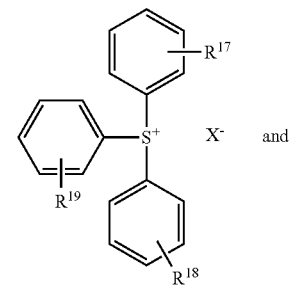 and

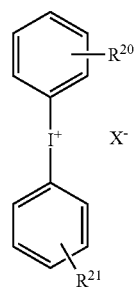

wherein $R^{16}$ is independently a hydrogen atom or a substituted or unsubstituted alkyl group, aryl group, or aralkyl group; $R^{17}$ to $R^{21}$ is independently a hydrogen atom, a halogen atom, a substituted or unsubstituted alkyl group having 1 to 10 carbon atoms, or a substituted or unsubstituted alicyclic hydrocarbon group; $X^-$ represents $OH^-$, $R^{22}OH^-$, or $R^{22}COO^-$; and $R^{22}$ is a monovalent organic group.

3. A radiation-sensitive composition, comprising:
(A) a low-molecular-weight compound having one or more acid-dissociable groups which decompose by the action of an acid to enhance solubility in an alkaline developing solution and one or more radiation-sensitive acid-generating groups which generate an acid upon application of an active ray or radiation per molecule, and having a polystyrene-reduced number-average molecular weight (Mn) measured by gel permeation chromatography (GPC) of 500 to 4,000, provided that compound (A) is not obtained from chain growth polymerization of a monomer with an unsaturated bond;
(B) a solvent; and
(C) a radiation-sensitive acid-generator other than the low-molecular-weight compound (A),
wherein the content of the low-molecular-weight compound (A) is 80 mass % or more of 100 mass % of the total solid component, and wherein the low-molecular-weight compound (A) is a compound shown by the following formula (1),

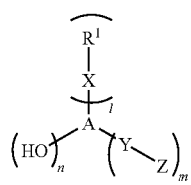
(1)

wherein A represents
(a) an aliphatic group having 1 to 50 carbon atoms,
(b) an aromatic group having 6 to 50 carbon atoms,
(c) an organic group consisting of said aliphatic and said aromatic group, or
(d) a group having a valence which is the sum of l+m+n and which has two or more of the (a), (b) or (c) groups;

X represents —O—, —CH$_2$C(=O)—O—, —C(=O)—O—, —OC(O)O—, or —Ar$^1$—O— (wherein Ar$^1$ represents a 1,4-phenylene group); R$^1$ represents an acid-dissociable group which is a substituted or unsubstituted tertiary hydrocarbon group having 4 to 12 carbon atoms or a substituted or unsubstituted acetal group; Y represents a single bond, —R$^2$—, —CH$_2$—C(=O)—O—R$^2$—, —C(=O)—O—R$^2$—, or —Ar$^2$—O—R$^2$— (wherein R$^2$ represents a substituted or unsubstituted methylene group or a substituted or unsubstituted alkylene group having 2 to 30 carbon atoms, and Ar$^2$ represents a substituted or unsubstituted 1,4-phenylene group); l is an integer from 1 to 4; m is an integer from 1 to 3; n is an integer from 0 to 10; Z is an organic group shown by any one of the following formulas (2) to (5) and, when m is 2 or 3, the organic groups may be either the same or different,

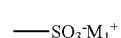
(2)

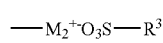
(3)

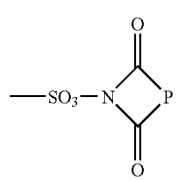
(4)

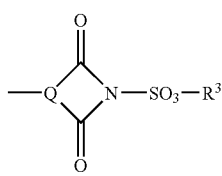
(5)

wherein M$_1^+$ in the formula (2) represents a monovalent onium cation, M$_2^+$ in the formula (3) represents a monovalent onium cation, R$^3$ in the formula (3) and the formula (5) represents a substituted or unsubstituted alkyl group having 1 to 15 carbon atoms or a substituted or unsubstituted aryl group having 1 to 15 carbon atoms, P in the formula (4) represents a substituted or unsubstituted alkylene group having 2 to 10 carbon atoms or a substituted or unsubstituted arylene group having 2 to 10 carbon atoms, and Q in the formula (5) represents a group shown by any one of the following formulas (6) to (8),

(6)

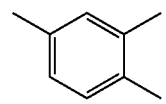
(7)

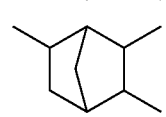
(8)

wherein the low-molecular-weight compound (A) is obtained by reacting a compound having an N-hydroxy-dicarboxylmide group and at least one of a phenolic hydroxyl group and a carboxyl group with a halogenated sulfonyl compound in the presence of a base.

4. The radiation-sensitive composition according to claim 3, further comprising an acid diffusion controller selected from the group consisting of

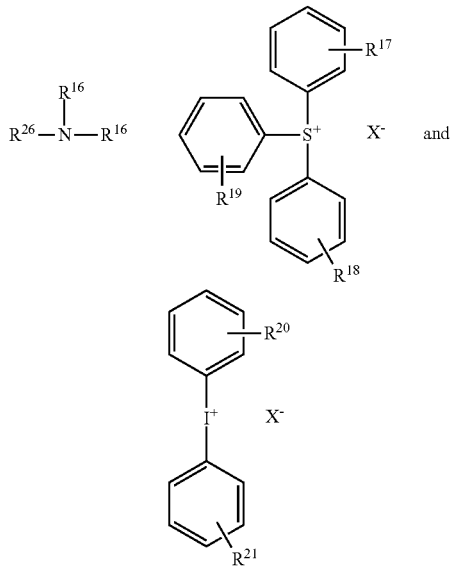

wherein R$^{16}$ is independently a hydrogen atom or a substituted or unsubstituted alkyl group, aryl group, or aralkyl group; R$^{17}$ to R$^{21}$ is independently a hydrogen atom, a halogen atom, a substituted or unsubstituted alkyl group having 1 to 10 carbon atoms, or a substituted or unsubstituted alicyclic hydrocarbon group; X$^-$ represents OH$^-$, R$^{22}$OH$^-$, or R$^{22}$COO$^-$; and R$^{22}$ is a monovalent organic group.

* * * * *